United States Patent [19]

Bernard et al.

[11] Patent Number: 4,883,063

[45] Date of Patent: Nov. 28, 1989

[54] PERSONAL MONITOR AND PROCESS FOR HEAT AND WORK STRESS

[75] Inventors: Thomas E. Bernard, Pittsburgh; Gary W. Sherwin, Yukon; William L. Kenney, Jr., Boalsburg; Debra A. Lewis, State College, all of Pa.

[73] Assignee: Electric Power Research Institute, Inc., Palo Alto, Calif.

[21] Appl. No.: 338,374

[22] Filed: Apr. 13, 1989

Related U.S. Application Data

[63] Continuation of Ser. No. 55,654, May 29, 1987, abandoned.

[51] Int. Cl.$^4$ ............................................. A61B 5/02
[52] U.S. Cl. ................................... 128/670; 128/706; 128/736
[58] Field of Search .............................. 128/670-671, 128/687-690, 736, 696, 706-708

[56] References Cited

U.S. PATENT DOCUMENTS

| | | | |
|---|---|---|---|
| 3,675,640 | 7/1972 | Gatts | 128/671 |
| 3,978,849 | 9/1976 | Geneen | . |
| 4,090,504 | 5/1978 | Nathan | . |
| 4,117,834 | 10/1978 | McPartland et al. | . |
| 4,129,125 | 12/1978 | Lester et al. | . |
| 4,308,870 | 1/1982 | Arkans | 128/736 X |
| 4,312,358 | 1/1982 | Barney | 128/670 |
| 4,367,752 | 1/1983 | Jimenez et al. | 128/707 X |
| 4,463,764 | 8/1984 | Anderson et al. | 128/671 X |
| 4,595,020 | 6/1986 | Palti | 128/736 |
| 4,679,566 | 7/1987 | Tamm | 128/671 |

FOREIGN PATENT DOCUMENTS 117330 9/1984 European Pat. Off. .

OTHER PUBLICATIONS

Journal A, vol. 24, No. 4, Oct. 1983, (Antwerpen, BE), M. Woerlee: "Measurements of Human Work and Work Environment", pp. 195-204, see pp. 196-198: 2. Measurements in the Blood Circulation During Work; FIGS. 2, 4; pp. 200-203; 5. Measuring the Thermal Loading During Work and 6. Measurement in the Work Environment.

*Primary Examiner*—Angela D. Sykes
*Attorney, Agent, or Firm*—Flehr, Hohbach, Test, Albritton & Herbert

[57] ABSTRACT

A personal monitor (10, 100, 200) for work and heat stress has a heart beat sensor (12) producing output electrical signals indicating a user's heart beats. A memory (127) stores heart beat information corresponding to the heart beat signals produced over predetermined time intervals. A microprocess (126) is connected to receive the heart beat information from the memory (127). The microprocessor (126) analyzes the heart beat information incrementally over the predetermined time intervals under program control to obtain a physiological demand during the predetermined time intervals and compares the obtained physiological demand against a stored physiological demand limit. Light emitting diodes (208) and a sound producing diaphragm (186) provide indications to the user when the stored physiological demand limit has been exceeded. The microprocessor (126) controls operation of the LEDs (208) and the diaphragm (186).

19 Claims, 12 Drawing Sheets

Minute of Delay

| | |
|---|---|
| 0 | Most Recent HR |
| 1 | |
| 2 | |
| 3 | |
| 4 | MTA-5 End Point |
| 5 | |
| • | |
| • | |
| • | |
| 9 | MTA-10 End Point |
| • | |
| • | |
| • | |
| 19 | MTA-20 End Point |
| • | |
| • | |
| • | |
| 29 | MTA-30 End Point |
| • | |
| • | |
| • | |
| 44 | MTA-45 End Point |
| • | |
| • | |
| 59 | MTA-60 End Point |
| • | |
| • | |
| 89 | MTA-90 End Point |
| 90 | One Minute Past Values for MTA-90 |

FIG.—11

| DATA | | ALERT THRESHOLD | | |
|---|---|---|---|---|
| | | Warning | Reset | Action |
| $T_d$ | $D_1$ | $W_1$ | $R_1$ | $A_1$ |
| MTA-5 | $D_2$ | $W_2$ | $R_2$ | $A_2$ |
| MTA-10 | $D_3$ | o | o | o |
| MTA-20 | $D_4$ | o | o | o |
| MTA-30 | $D_5$ | $W_m$ | $R_m$ | $A_m$ |
| MTA-45 | $D_6$ | o | o | o |
| MTA-60 | $D_7$ | o | o | o |
| MTA-90 | $D_8$ | $W_8$ | $R_8$ | $A_8$ |

FIG.—12

PERSONAL MONITOR AND PROCESS FOR HEAT AND WORK STRESS

This is a continuation of application Ser. No. 055,654, filed May 29, 1987, now abandoned.

BACKGROUND OF THE INVENTION

1. Field of the Invention

This invention relates to a device and process which helps a user avoid excessive heart rates and increases in body temperature during heat stress and heavy work exposures. More particularly, it relates to a device and process that measures physiological responses to work and heat stress and provides recommendations to the user in real time. Most especially, it relates to such a device and process in which the user is provided the recommendations to make an intelligent decision to control his or her exposure to the stress. It further relates to such an apparatus and process which is useful in an industrial environment.

2. Description of the Prior Art

Two approaches are conventional to avoid excessive heart rates and increases in body temperature during heat stress exposures. One is to limit the exposure through administrative controls, such as stay times. The other is to use self-determination. Stay times are usually very conservative to protect most people. Self-determination often leads an individual to overextend himself or herself.

A variety of measuring devices are known in the art for measuring exertion and related parameters. Body core temperature is a basic physiological measure of the body's response to heat stress. Rectal temperature is commonly accepted as a primary measure. Because rectal temperature is measured by an inserted probe, it is not practical or acceptable for routine evaluation of core temperature. A substitute measure is required.

Commonly used substitutes for rectal temperature are ear, esophageal, and oral temperatures. While the temperature measuring technology for these is readily available, they pose many practical problems that make them unsuitable for a personal monitor. Swallowable or ingested thermotransmitters are possible, but unsuitable because of cost, potential liability and questionable acceptability.

A commercially available device can predict body core temperature by equalizing the heat flux from the core to the surface by placing a heater on the outside. However, this device requires too much power to be fully practical in this application, and it would give erroneous results in high ambient temperatures.

Heart rate is another physiological measure that is related to work and heat stress. There are several commercially available devices to measure heart rate in work environments. The primary markets for these devices are sport, exercise and rehabilitation. While the methods and embodiments vary somewhat, the primary method of monitoring is to provide a low and high threshold for heart rate, so that an alarm can be given if heart rate goes below or above the specified window.

For industrial environments, the low threshold does not have any real purpose. The high threshold is more valuable. If a person's heart rate exceeds the threshold, an alarm can warn him or her of possible overexertion. The problem with these high threshold warnings is how to set the threshold. Workers can and do have momentary peaks of high heart rates due to sudden bursts of activity or isometric work. These peaks do not represent sustained levels of work, but they result in an alarm that would be reasonable for sustained levels of high demand. However, with a simple high threshold, there would be many alarms that do not represent significant physiological strain. The situation is further complicated by prolonged work at an intermediate level. The high threshold would miss prolonged heart rates just below the threshold that are very significant physiological strains.

Examples of prior art devices for measuring heart rates, body temperature and related parameters are disclosed in the following issued U.S. Pat. Nos.: 4,513,753, issued Apr. 30, 1985 to Tabata et al.; 4,450,843, issued May 29, 1984 to Barney et al.; 4,425,921, issued Jan. 17, 1984 to Fujisaki et al.; 4,409,985, issued Oct. 18, 1983 to Sidorenko et al.; 4,378,111, issued Mar. 29, 1983 to Tsuchida et al.; 4,367,752, issued Jan. 11, 1983 to Jimenez et al.; 4,343,315, issued Aug. 10, 1982 to O'Leary and 4,312,358, issued Jan. 26, 1982 to Barney. The state of the art is further indicated by Humen, D.P. and Boughner, D.R., "Evaluation of Commercially Available Heart Rate Monitors," *The Canadian Medical Association Journal*, Vol. 131, Sept. 15, 1984, pp. 585–589 and by commercially available heart rate monitors from Computer Instruments Corporation, Hempstead, L.I., N.Y. 11550; Biosig Instruments, Inc., Champlain, N.Y. 12919 and Dak Industries, Inc., Canoga Park, CA 91304.

While the art relating to such devices is therefore a well-developed one, a need still remains for a personal monitor and process capable of meeting the demands of an industrial environment.

SUMMARY OF THE INVENTION

Accordingly, it is an object of this invention to provide a personal monitor and process for work and heat stress which will measure physiological responses to the stresses and provide recommendations to the user in an industrial environment.

It is another object of the invention to provide such a personal monitor and process which will neither provide the user with a multitude of inappropriate warnings, nor allow the user to exceed safe limits without providing a warning to the user.

It is a further object of the invention to provide a novel sensor for measuring body core temperature.

It is still another object of the invention to provide such a personal monitor and process which combines measurements of different body parameters to provide reliable indication of work and heat stress to the user.

The attainment of these and related objects may be achieved through use of the novel personal monitor, temperature sensor and process of this invention. A personal monitor for work and heat stress in accordance with this invention has a heart beat sensor producing output electrical signals indicating a user's heart beats. Means in the personal monitor stores heart beat information corresponding to the heart beat signals produced over a predetermined time interval and is connected to receive the heart beat information. An information processing means is connected to receive the heart beat information from the storing means. The information processing means is configured to analyze the heart beat information incrementally over predetermined time intervals to obtain a physiological demand during the predetermined time intervals and to compare the obtained physiological demand against a stored physiological demand limit. A means provides an indication to the user when the stored physiological demand limit has been exceeded. The information processing means is configured and connected to control operation of the indication providing means.

A temperature sensor in accordance with the invention has a thermally conducting member with a surface configured to make direct contact with an object the temperature of which is to be measured. A device is thermally connected to the thermally conducting member for producing an output electrical signal which is a function of temperature. A body of thermally insulating material surrounds a remainder of the thermally conducting member.

A process for monitoring heat and work stress of an individual in accordance with the invention includes measuring the individual's heart beats. The heart beat information is analyzed incrementally over predetermined time intervals to obtain a physiological demand during the predetermined time intervals. The obtained physiological demand is compared against a predetermined physiological demand limit. An indication to the individual is provided when the predetermined physiological demand limit has been exceeded.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 11 is a diagrammatic representation of certain information stored and used in operation of the invention.

FIG. 12 is a diagrammatic representation of certain other information stored and used in operation of the invention.

DETAILED DESCRIPTION OF THE INVENTION

Physiological Basis

Figure 1:
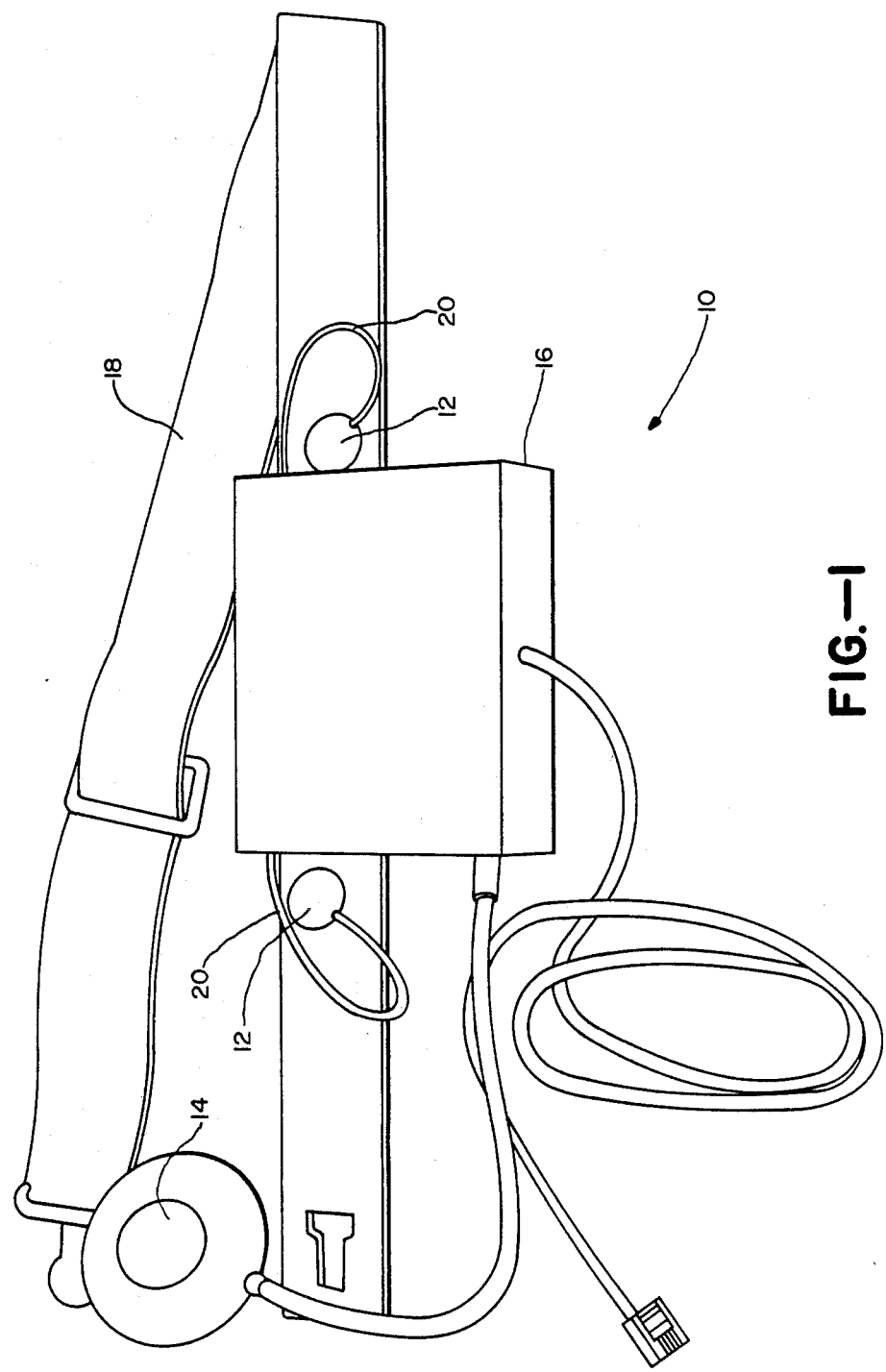
FIG. 1 is a perspective view of a first portion of a personal monitor in accordance with the invention.

This section describes the physiological basis on which the PM algorithm was based. Physiological strain is the body's response to a stress. The stress in heat stress is the combination of work demands, clothing requirements and the environment. In addition to sweating, the most apparent physiological strains in response to heat stress are body temperature and heart rate. Basically, the accumulation of heat is reflected in body temperature while the ability to perform work and dissipate heat is reflected in heart rate. While body core temperature and heart rate correlate with each other, they measure different physiological strains, and therefore add information about physiological state when both are considered. The Personal Monitor (PM) attempts to account for both body temperature and heart rate in order to present an alert for excessive physiological strain. Based on laboratory evaluation there is also evidence the PM is sensitive to the onset of symptoms which is also reason to terminate a heat stress exposure.

The algorithm uses insulated skin temperature and heart rate history to determine the alert state. These two physiological measures are treated independently and the alert state is determined by the measure that reaches the alert threshold first.

The insulated skin temperature (called disk temperature) is a physiological variable developed to predict overexposure to heat stress as a surrogate measure for body core temperature. There is a very high correlation between core temperature under two different conditions of heat stress.

The next step is to establish a safe limit for core temperature. The National Institute for Occupational Safety and Health (NIOSH) and the World Health Organization have recommended limiting heat exposure so that core temperature does not exceed 38.0° C. for daily, prolonged periods, i.e., for chronic work under heat stress conditions. WHO suggested that "in closely controlled conditions the deep body temperature may be allowed to rise to 39° C. (102° F.)". There is an increased risk for heat illness at the higher core temperature as well as increasing incidence of unsafe behavior linked to heat stress. Heat stroke is associated with core temperatures above 40° C.

The action alert threshold for core temperature was selected to be 38.5° C., because the PM represents a means to closely control the heat stress exposure and the alert threshold allows time to terminate the exposure. First, this limit allows a greater exposure to heat stress above acceptable levels for chronic exposures. Second, it allows five to ten minutes to leave an area of heat stress.

With a core temperature limit of 38.5° C. specified, a disk temperature threshold for the alert could be determined. To set an action alert threshold for disk temperature that protects most workers from exceeding a core temperature of 38.5° C., two decisions were made. First, analysis indicated that the relationship of core temperature to disk temperature is different for different clothing. For this reason, two classes of clothing were defined: (1) work clothes or single cotton coveralls, and (2) double cotton coveralls or impermeable clothing (plastics) over coveralls. Second, disk temperature is not an exact measure of core temperature, but a surrogate. This means that there is a certain amount of error associated with limiting core temperature by disk temperature. For each clothing class or ensemble, a disk temperature was selected so that for 95% of the cases core temperature was less than 38.5° C. The selected disk temperature was the action alert threshold. The action threshold for work clothes or cotton coveralls is 38.2° C., and for double cotton coveralls or impermeable coveralls over cotton coveralls, it is 38.5° C. These values are the action alert thresholds in the PM algorithm, which indicate a time to terminate the exposure.

The design objectives for the PM called for a warning alert to give preliminary notice that there has been an increase in physiological strain, and reset criteria that would allow the alert status to change from warning to acceptable. The warning alert should allow about 10 minutes warning prior to an action alert under typical conditions of heat gain. The warning thresholds were 38.0° and 38.1° C. for work clothes/cotton coveralls and double cottons/impermeable clothing, respectively. If the strain is reduced after a warning alert, the PM will reset to the acceptable indicator. The reset thresholds were set to be 0.2° C. less that the warning level. The 0.2° C. drop indicates a significant drop in temperature and avoids problems with temperature sensor fluctuation or toggling around the threshold (e.g., changing between 37.9° and 38.0° C.).

The purpose of the heat rate criteria is to relate the information gained from monitoring heart rate to the cardiovascular strain of heat stress exposure. This is accomplished by examining the relationship between work demand and endurance time, then relating endurance time and heart rate through work demand, and finally proposing heart rate criteria to mark extensive strain. In addition, recovery heart patterns can be used to judge the level of cardiovascular adjustment to heat and work stress.

As a person performs physically demanding work, the muscles demand oxygen, which is delivered by circulating blood. The increased demand for oxygen and, therefore blood flow, is achieved by increasing the heart rate. As work demands increase, oxygen demand increases to support muscle metabolism and heart rate rises to increase blood flow. If a person is subjected to increasing levels of work (and oxygen demands), his or her heart rate will reach a maximum value, which is also marked by a maximum utilization of oxygen (or maximum aerobic capacity, MAC).

A common observation is that the same task can be easily performed by one worker while another will have difficulty. The relative difficulty of performing a work task depends on how the oxygen demand of the task compares to the individual's MAC. For work demands and commensurate oxygen demands less than the MAC, the relative difficulty is related to the oxygen demand expressed as the percent of the maximum aerobic capacity (%MAC). A very fit worker (high MAC) will have less difficulty performing the same task than a less fit one because the former worker will be working at a lower fraction of his MAC.

If the work requires an oxygen demand that is 30% of the maximum, the task is considered light and can be done for hours, but if it is 75% of the MAC, the task can only be performed for about 20 minutes under a great deal of physical duress that will lead to exhaustion. Many laboratory studies have been performed to examine the relationship between time to exhaustion (endurance time) and % MAC. In the typical study, an individual is given a constant work task requiring a steady rate of oxygen consumption (e.g., treadmill walking or pedaling a bicycle-ergometer). The work is performed until exhaustion, and the time is noted. The endurance time plotted against % MAC gives similar curves for all individuals. Endurance time decreases exponentially with % MAC.

An average person can work about 20 minutes at 80% of his/her MAC before exhaustion. This increases to 40 minutes at 70% MAC and 80 minutes at 60% MAC. From the job design point of view, the job should not require more time than the endurance time. So a work task requiring 70% MAC of a person should not exceed 40 minutes. Alternatively, if a minimum work time is required, the actual % MAC must be lower than that % MAC associated with the endurance time that equals the work time. For instance, if 40 minutes are required to perform a task, the actual % MAC should be less than 70% MAC for any worker who is expected to complete the task.

There is a range of endurance times (ET) for any particular value of % MAC. In order to be protective of most of the population, a conservative line can be drawn to include all of the ET data for a given % MAC, which follows the equation $$log_{10}(ET) = 4.0 - 4.0(\% MAC/100\%) \qquad (1a)$$

$$\% MAC = 25\%[log_{10}(ET) - 4.0] \qquad (1b)$$

where ET is endurance time in minutes and the term (% MAC/100%) is the ratio from 0 to 1 that the oxygen demand is to the MAC. Equations 1a and 1b are the same relationship expressed in two ways. The meaning of the relationship can be interpreted as follows. For any given % MAC, most workers would be able to perform at that relative level of work for at least a time of ET from Equation 1a. Or, if a work demand required a time of ET, it can be done by anyone who is working at or below the respective value of % MAC from Equation 1b. So a worker can work at least 10 minutes at 75% MAC; or a job requiring 10 minutes of work can be performed by anyone working at or below 75% MAC.

As a practical note, a pattern of different work demands with different oxygen demands can be averaged together over a time interval, and the average %MAC computed. The average % MAC is used to estimate the expected endurance time, and this endurance time is compared to the actual time requirement (the time base for the average). For instance, 5 minutes at 80% MAC can be averaged with 20 minutes at 50% MAC for an average demand of 56% MAC over 25 minutes. This average rate can be sustained because it is less than the endurance time of 100 minutes associated with 56% MAC. This averaging technique cannot be used if the work demand in a shorter period would mean the endurance time is exceeded. For instance, 30 minutes at 80% MAC cannot be averaged with 30 minutes at 40% MAC for an average of 60% MAC over 60 minutes. The individual would reach exhaustion during the 80% MAC segment, because the endurance time for 80% MAC is twenty minutes.

Based on this averaging principle, an incremental analysis can be performed to assess whether a job may cause exhaustion. In the incremental analysis, the relative oxygen demands (% MAC) over small intervals (i.e., 5 minutes) are examined to determine if the associated endurance time is less than the time interval. That is, for any 5 minute interval, the average % MAC should not exceed 83 for the individual as calculated from Equation 1b, using 5 minutes for ET. The time step is then increased (e.g., 10 minutes) and the average % MAC for that interval is calculated. Once again, if the average % MAC is less than 75% MAC (value from Equation 1b for ET=10 min), there should not be any excessive physiological demand (exhaustion). By incrementing the time base of the average out to the working time itself, all possible combinations of work can be examined in terms of their effect on exhaustion. This means that short periods of high demand are considered as well as long periods of lower average demands.

Because of the exponential nature of the relationship, the time intervals can be increased geometrically to reduce the number of averaging intervals without losing protective ability. So starting at 5 minutes, which is the smallest practical interval, the intervals can follow 10, 20, 40, 80, . . . - minutes. As an approximation of the geometric progression, 7 averaging intervals were selected for the PM algorithm: 5, 10, 20, 30, 45, 60, and 90 minutes. From Equation 1b, the highest % MAC that can be sustained for these intervals is 83, 75, 67, 63, 59, 56, and 51 % MAC, respectively. For work scenarios where the PM would be used, there is no need to extend the averaging intervals beyond 90 minutes because few exposures will go to 3 hours (180 minutes) of steady work.

The next step to developing an algorithm for heart rate is to relate heart rate to % MAC. This step is required because it is not feasible to know the MAC of each potential user of the personal monitor as well as the oxygen demands for all possible tasks to be performed so that % MAC can be known.

As a person moves from a resting oxygen demand to MAC, heart rate increases from the resting rate ($HR_{rest}$) to the maximum heart rate ($HR_{max}$) The average resting heart rate is 75 beats per minute, and does not change much for age, race or sex. For the general population, $HR_{max}$ decreases with age, and is reasonably well predicted by:

$$HR_{max} = 220 - age(years) \qquad (2)$$

An implication of equation (2) for the population at large is that the average $HR_{max}$ for a given age is 1 beat per minute (bpm) less than those a year younger. This also means average MAC decreases because of a lower ability to deliver blood and oxygen to the muscles, as is the case.

Heart rate reserve (HRR) is the difference between $HR_{rest}$ and $HR_{max}$. Any heart rate (HR) can then be expressed as percent heart rate reserve % HRR by:

$$\%HRR = [(HR_{max} - HR)/(HR_{max} - HR_{rest})] \times 100\% \qquad (3a)$$

or $$\%HRR = [(HR_{max} - HR)/HRR] \times 100\% \qquad (3b)$$

% HRR is zero at rest and 100 at $HR_{max}$.

There are three factors to consider: (1) MAC(100% MAC) occurs at $HR_{max}$, (2) the oxygen demand is about 10% MAC, and (3) heart rate increases linearly with % MAC. These three facts suggest a basic approximation used in the PM: % HRR is equal to % MAC. If someone is using 50% of his MAC to do work, he will also use 50% of his HRR. To illustrate these relationships, suppose a 45 year old worker performs a task with a heart rate of 125 beats per minute (bpm). First, his $HR_{max} = 175 (=220-45$, Equation 2) and he has a resting rate of 75. He has an HRR of 100 bpm (175-75=100). If his heart rate is 125 bpm, he is using 50% of his HRR($[(175-125)/100] \times 100\%$, Equation 3b). This means he can work for at least 100 minutes (Equation 1a). Knowing HR then allows the endurance time to be estimated through % HRR and % MAC. This demonstrates that it is not necessary to know the oxygen demand of the task or the individual's MAC to be able to estimate endurance time—only heart rate for the task.

The relationships can be used in reverse as well. If a minimum work time is known and equated to ET, the highest expected work demand expressed as % MAC can be estimated from Equation 1b, and therefore the % HRR. With the % HRR and assumptions about $HR_{rest} (=75)$ and $HR_{max}$ (Equation 2), a limit on heart rate can be suggested. As an example, suppose the work time is 20 minutes and the worker is 45 years old (as above). The highest % MAC is 67 for ET=20 from Equation 1b. This then means that the average heart rate for the 20 minutes should not exceed 67% HRR. Equation 4 is a rearranged version of Equation 1b.

$$HR = HR_{rest} + HRR(\% HRR/100\%) \qquad (4)$$

Sixty-seven % MAC translates to a heart rate of 142(=75+100[67/100]), Equation 4.

The preceding discussion, however, has not addressed heat stress. It is known that the added burden of heat stress on the cardiovascular system is also reflected in heart rate, and that heart rate increases due to heat stress can be treated as an increment in % MAC. In other words, the physiological strain reflected in heart rate is the same whether the heart rate is due to work alone or a lesser level of work in combination with heat stress. Therefore, the effect of work and heat stress on heart rate are additive, and the overall effect on heart rate can be used to estimate a % MAC through % HRR. The % MAC can then be used to predict a maximum work time or endurance time.

Two assumptions come into play, therefore, in using heart rate to monitor physiological strain due to work under heat stress. First, the effects of heat stress on heart rate are additive to the heart due to work alone. Second, heart rate can be used to reflect the equivalent % MAC and thus the endurance time is short for high % MAC and increases with lower values of % MAC. The resulting principle is that high heart rates (high demands, reflected as the combination of metabolism and heat stress) can be safely sustained for short periods of time and lower heart rates (lower demands) for longer periods.

For the PM, a heart rate threshold is a level above which an average heart rate for a specified period of time triggers an alert. For a short time, the PM should tolerate a high heart rate due to heavy work and/or high heat stress. This can be achieved by using a short averaging period with a high threshold. In contrast, the PM must be sensitive to a moderate demand (lower HR) over a longer period. Therefore, a longer averaging period can be used with a lower threshold.

Averaging avoids problems commonly found with single, static thresholds used in currently available heart rate monitors. If a static criterion is set high enough to allow bursts of high demand, then it will miss longer terms of moderate strain. If it is set low for moderate strain, it will alarm for brief, but allowable, levels of high demand. The PM accounts for the continuum of strains between these two situations by employing multiple averaging periods. Thresholds can be selected for each of the multiple averaging periods for heart rate.

Multiple averaging periods and thresholds are calculated and updated through the technique of moving-time-averages (MTAs) of heart rate. The application of MTAs represents a novel approach for heart rate monitoring. An MTA-5 (moving-time-average over 5 minutes) represents the average heart rate for the past five minutes, and can be used to examine a burst of high demand. If a heart rate is high for a couple of minutes, the MTA-5 will quickly approach the high rate. When it reaches a critical value, it will cause an alert. But if the burst of high demand is too short to cause a concern, the MTA-5 will not reach the critical level. In this way, it can be sensitive to high demands without overreacting to brief transients. At the other extreme is an MTA-90 (90 minute moving-time-average). Even sustained levels of high heart rate are hidden, but gradual increases due to long term, moderate demands that will cause fatigue are accounted for. A threshold or critical value for MTA-90 can be much lower, without causing an alert until the long-term demand is judged excessive.

The PM uses 7 MTAs on time bases of 5, 10, 20, 30, 45, 60 and 90 minutes to provide a steady progression of protection from short term, high demands to long term, moderate demands. The MTA intervals were taken as an approximation of a geometric progression (successive doubling) from 5 minutes.

The effects of moving time averages on smoothing out peaks and identifying trends can be seen in the following example. Consider an operations supervisor performing an inspection of the containment building of a nuclear power plant immediately following a hot shutdown. This requires much ladder and stair climbing (high heart rates) as well as relative inactivity. MTA-5 follows the short-term trends of HR very well without being unduly influenced by very short peaks. MTA-90, on the other hand, follows the steadily increasing cardiovascular load caused by the long-term effects.

The action alert thresholds for the MTAs were selected using two factors: (1) age for adjustments in $HR_{max}$ and (2) % MAC for an endurance time equal to the time base of the averaging period. Three age groups were judged to be sufficient to reflect the effects of age on $HR_{max}$. Two groups would not account for effects of age, and the variation in $HR_{max}$ for a given age defeats any advantage of more groups. HRRs were then estimated for each group assuming a typical resting rate of 75 bpm and an $HR_{max}$ for the midrange age. The groups with respective HRRs and midrange age are:

*Young: <35 years with HRR=118(27 years)
*Middle: 36-50 years with HRR=102(43 years)
*Older: >51 years with HRR=87(58 years)

For each MTA time base, ET was set to the time base and the % MAC (and hence the % HRR) was calculated from Equation 1b. For the 7 averaging intervals 5, 10, 20, 30, 45, 60, and 90 minutes, the highest % MACs that can be sustained for these intervals are 83, 75, 67, 63, 59, 56, and 51 % MAC, respectively. For each age group, the heart rate for each % HRR, which equals % MAC, was calculated using Equation 4. This was taken as the action alert threshold. The heart rate thresholds for the older age group were adjusted downward by about 2 bpm based on the laboratory tests and other data that suggest a greater loss of ability to cope with heat stress than would be expected from an age related decrement in cardiovascular capacity.

The warning alert thresholds were selected to give about 10 minute warning to the action alert threshold if the heart rate was maintained at moderate demands. The reset levels were selected to indicate a sustained drop in heart rate from the warning levels. They appear to be adequate from the laboratory tests. The following table gives the three alert thresholds for the different age groups and MTA time bases as finally selected for the PM.

Heart rate recovery patterns were introduced by Brouha at duPont as a method to evaluate the physiological strain experienced by an individual performing physically demanding work. They also apply to conditions of heat stress. The criteria were revised by Fuller and Smith. The recovery heart rate method requires a worker to stop working and sit down for 3 minutes. Three 30 second pulse counts($P_n$) are taken during the second half of each successive minute as follows:

*$P_1$: 30 to 60 seconds after sitting
*$P_2$: 90 to 120 seconds after sitting
*$P_3$: 150 to 180 seconds after sitting Each of the three pulse counts are doubled to give a pulse rate. Fuller and Smith found that a $P_3$ rate less than 90 bpm indicated full recovery and that the preceding work did not have an excessive demand; that is, it was acceptable.

If $P_3$ was greater than 90, the worker was accumulating a physiological debt with the implication that he cannot continue indefinitely. Looking further, if the drop from $P_1$ to $P_3$ is greater than 10 bpm, the recovery is marginal. This means he can continue to work, but exhaustion may occur later. This is analogous to the warning alert. If the drop is less than 10 bpm, there is no recovery and work should cease, equivalent to an action alert.

Based on the laboratory data for recovery patterns near the termination point, the above procedure was further modified. A "no recovery" category is assigned by the PM algorithm if $P_3$ is greater than 120, regardless of the difference from $P_1$.

Hardware

The personal monitor (PM) is comprised of three distinct components: sensor module, monitor module and alert module. Each of these will be described in detail.

The sensor module 10 is shown in FIG. 1. The sensor module 10 contains EKG sensors (electrodes) 12, temperature disk (insulated skin temperature) 14, and an electronics package 16 for the sensors 12 and 14. The sensor package 16 is mounted on a harness 18 worn on the chest. Placed on the inside of the harness 18 are the EKG electrodes 12 and the temperature disk 14, all of which must be in contact with the skin.

The primary goal in the selection of the EKG electrodes 12 was to select or design ones that could be used to obtain a good EKG signal with a minimum amount of skin preparation. Good readings can be obtained if the impedance between the two electrodes 12 is lower than 10K ohms.

The electrodes 12 selected for the personal monitor are commercially available as an integral part of a chest strap harness 18. This strap 18 is part of an exercise heart rate monitor developed by AMF and marketed by Computer Instruments Corporation. It uses two flexible conductive materials segments about 3 cm×6 cm on the inside of the strap 18 for the electrodes 12. A button snap through the material and the harness 18 establishes an electrical connection to the outside. The PM sensor module 10 uses leads to the button snaps for the EKG electrodes 12.

If the electrodes 12 are simply placed on the chest over dry skin, the impedance is too high (>10K ohms) to obtain a good EKG. After a couple of minutes, enough sweat has accumulated under the electrodes 12 to reduce the impedance to acceptable levels. To obtain an acceptable EKG signal immediately, a small amount of conducting lotion or water can be spread on the electrodes 12 before donning them. No skin preparation (e.g., rubbing, cutting away hair, etc.) is necessary.

Alternative electrodes that can be used in place of the electrodes 12 are the pregelled, disposable type frequently used in hospitals and for exercise stress tests. The basic concept is a soft foam disk with adhesive surface that is used to attach the electrode to the person. The center of the disk has a conductive jelly to form an electrical contact with the skin. A third type of electrode that could be used is a conductive gelatin type used with an exercise heart rate monitor by Biotechnology, Inc.

Three electrodes (active, reference and ground) are needed to measure the EKG. The active electrode 12 is placed over the heart (left side of the chest). The reference electrode 12 is placed on the right side of the chest. The temperature disk 14 also serves as the ground electrode, and it is placed outside of the line formed by the reference and active electrodes 12. In this fashion, the copper disk is both a thermal and electrical conductor.

The harness 18 is easily donned and doffed by one person. Generally, it is then slid into correct position on the chest and the temperature sensor 14 is inserted under the harness 18 on the right side. The harness 18 can be hand washed to sanitize it.

Figure 2:
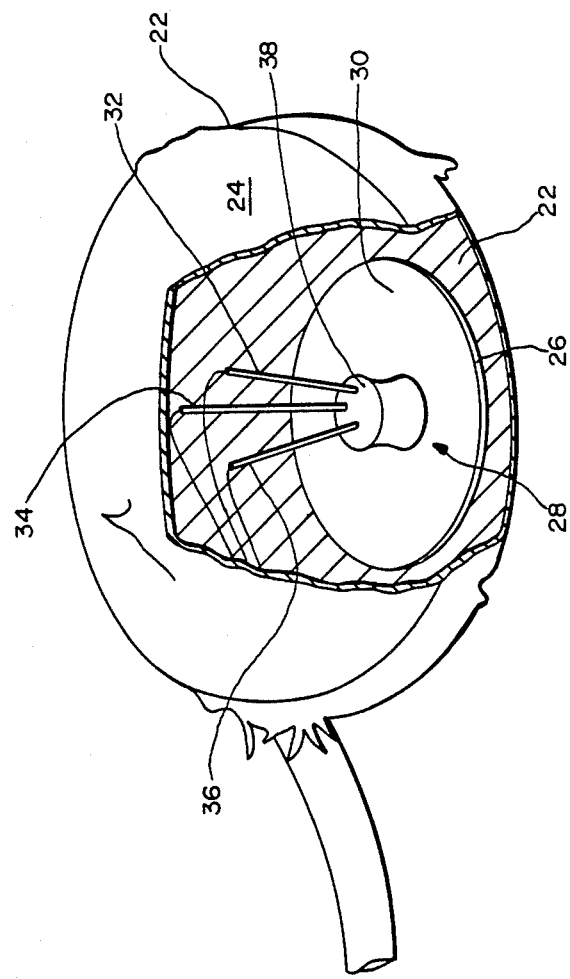
FIG. 2 is a perspective view of a second portion of the personal monitor, with a partial cutaway to show interior detail.

The temperature sensor 14 is shown in FIG. 2. A styrofoam disk 22 is 0.8 cm thick with a 4.2 cm diameter is the insulating body of the sensor. On the surface 24 facing the skin there is a 2.5 cm diameter copper disk 26. A temperature sensitive solid state device 28 (National Semiconductor LM34CA) is soldered to the internal side 30 on the copper disk 26 and surrounded on the other sides by the styrofoam disk 22. The solid state temperature sensor 28 has a low output impedance and a linear voltage output proportional to temperature (T) as expressed by:

voltage (mV) = 10 × (temperature in °F.).

For example, the output is 0.950 V at 35° C. (95° F.) and is 1.040 V at 40° C. (104° F.), for a change of 90 mV over the range of typical disk temperatures. If desired, a thermistor could also be used, but the solid state device 28 has a comparable temperature sensitivity, is more rugged, and has a lower power requirement.

There are three electrical leads 32, 34 and 36 from the temperature sensor 28. The first lead 32 is the electrical common (ground) lead that is connected to the metal case 38 of the sensor. This lead 32 is also used as an electrical conductor in its role as ground electrode. The second lead 34 is for the supply voltage (+5 volts). The third lead 36 is the voltage output, which is proportional to temperature.

Figure 3:
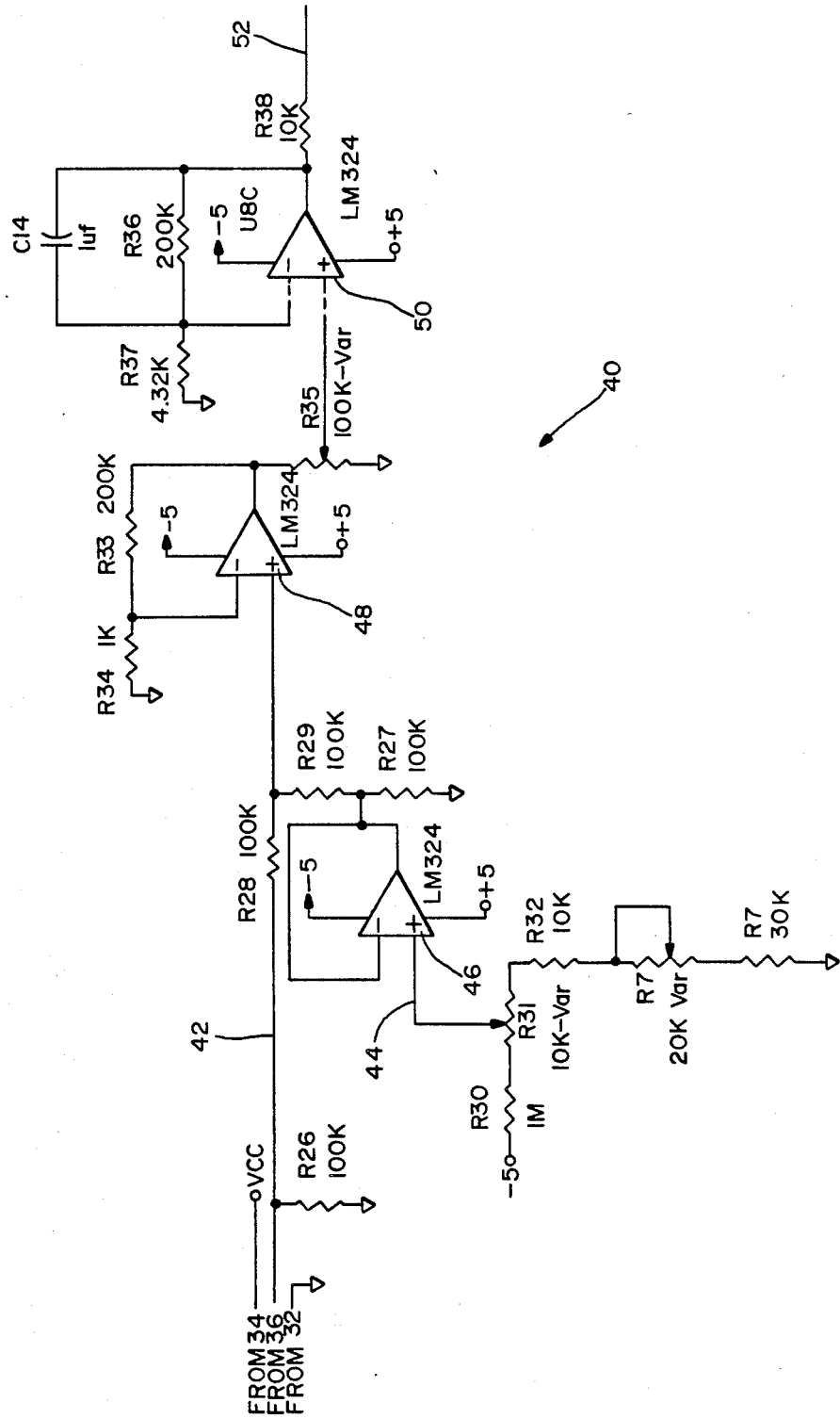
FIG. 3 is a schematic diagram of a first electrical circuit used in the portion of the personal monitor shown in FIG. 1.

Sensing circuit 40 is shown in the diagram of FIG. 3. The first step is to sum the voltage output from the device 28 on line 42 with a bias voltage on line 44 in summing amplifier 46 so that a zero adjustment is available. Using the adjustable resistors R31 and R7, a nominal bias voltage of −975 mV is summed with the temperature device output voltage so that the voltage entering amplifier 48 is zero when the device is at 36.4° C. (97.5° F.).

Another variable resistor R36 is used to adjust the gain of amplifier 50. The amplifier 50 gain is set so that a one bit change in an analog-to-digital (A/D) converter in the monitor module is equivalent to 0.025° C. The monitor module has an 8-bit A/D converter over a range of 0 to +5 volts, which means that it gives an numerical value for 0 for 0 volts and 255 for +5 volts. That is, there are 51 output units per volt input to the A/D converter. Using the target sensitivity of 0.025° C./unit, an increase of 3° C. over 36.4° C. (or 39.4° C.) should have an A/D reading of 120 (=3/0.025). The gain is adjusted so that a temperature of 39.4° C. on the device 28 will yield 2.353 volts (5×120/255) at the amplifier 50 output 52. The amplifier output is the input to the A/D converter. The device 28 is calibrated with a water bath over the important range of temperatures (37° to 39° C.), and the calibration curve is placed in nonvolatile memory (EEPROM) as the slope and intercept of a least squares fit.

The role of the sensor module 10 in the determination of heart rate is to detect the occurrence of a heart beat and send a signal the the monitor module when one occurs. Heart rate detection circuit 60 in FIG. 4 relies on being able to detect the occurrence of a QRS complex, which is a very distinctive part of the EKG. It is a rapidly changing wave with a high amplitude (usually between 2 and 5 times larger than the other, more slowly changing waves).

Figure 4:
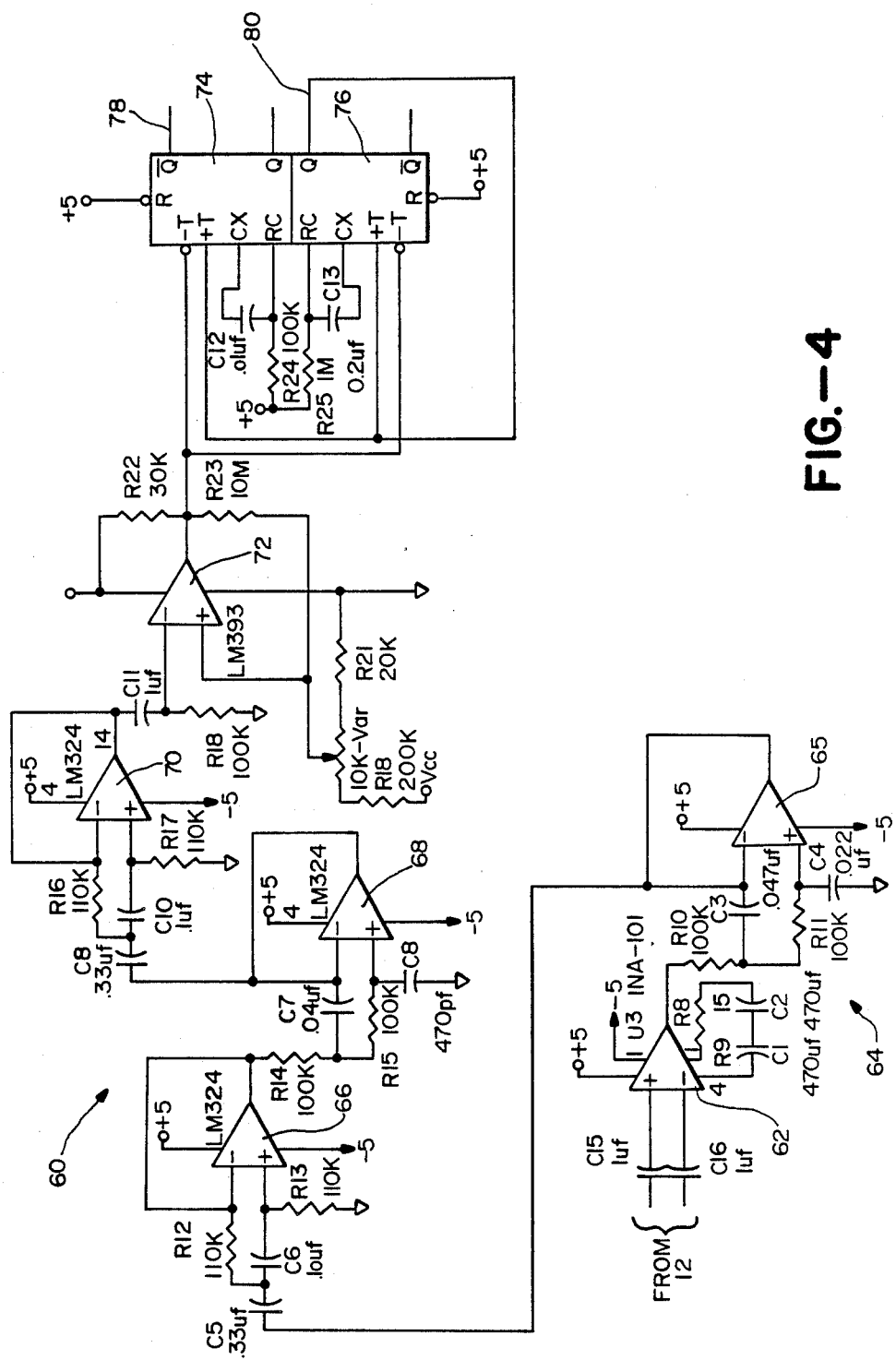
FIG. 4 is a schematic diagram of a second electrical circuit used in the portion of the personal monitor shown in FIG. 1.

As mentioned above, there are three electrodes involved. One is the ground electrode 14, which is also the temperature disk. It is connected to the instrument ground and provides stability to the signal. The other two electrodes are the positive (active lead) and negative (reference lead) inputs from EKG sensors 12 to an instrumentation grade differential amplifier 62 (Burr-Brown) as shown in FIG. 4. The signal is amplified by a factor of 1000 (from millivolts to volts) and is also passed through a relatively broad bandpass filter 64. The signal then passes through four active filters 65, 66, 68 and 70 that together provide a narrow bandpass filter designed to allow the moderate frequency (nominally 100 Hz) QRS wave to go through, while blocking lower frequency EKG waves, electrical noise, such as 60 Hz electrical noise in the environment, baseline drift due to changing electrode impedance and any higher frequency noise, such as 400 Hz instrumentation noise. The filter cutoff frequencies were designed empirically. The cutoff frequencies for the bandpass filter were adjusted by looking at the effect on the QRS wave. The frequency of the two high pass filters was increased until the amplitude of the QRS was affected; and in a similar manner, the frequency of the two low pass filters was lowered. The filtered EKG/QRS signal is then sent to a high gain comparator amplifier 72 that has a zero output until the input reaches a predetermined level. If the signal goes above that level, the output goes very quickly to +5 volts. Thus, when the QRS signal reaches the threshold, the amplifier 72 sends out a positive square wave to trigger a pair of monostable multivibrators 74 and 76.

The mulitivibrator circuit 74 provides a steady high signal (+5 volts) until the input trigger receives a positive pulse. The positive pulse triggers the beginning of a zero volts square wave from multivibrator 74 output 78. The output 80 of the other multivibrator 76 stays high for about 250 msec, which prevents triggering the first multivibrator 74. The relatively long high window of the second multivibrator 76 prevents a triggering of the first multivibrator 74 at frequencies above 255 times per minute, which is higher than any heart rates that will be observed. In addition to advancing a counter (see monitor module electronics), the low pulse from the first multivibrator output 78 allows LEDs 208-212 (FIG. 9) to blink with each heart beat (see alert module electronics). The width of the pulse to the LEDs was selected so that there is a discernible flash on the LEDs.

Figure 5:
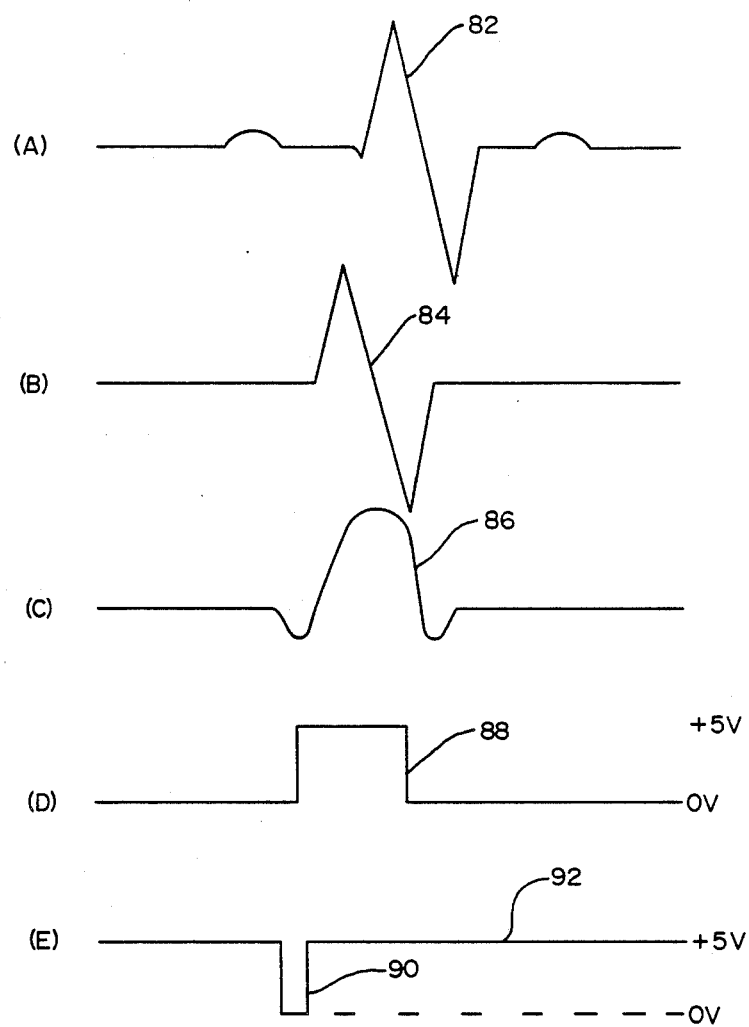
FIG. 5 are waveform diagrams useful for understanding operation of the electrical circuit of FIG. 4.

FIG. 5 illustrates the effects of the detection circuitry 60 on the EKG signal. At the top, the raw EKG signal 82 for one heart beat is shown. After passing through the first, broad bandpass filter 64, the signal has a sharp, bipolar character, illustrated at 84 in (b). The four stage, narrow bandpass filter 65-70 removes the negative component and the slow waves, and broadens the positive wave, as shown at 86 in (c). The signal then goes to the comparator 72 from which the filtered signal creates a square wave 88, as shown in (d). This highly conditioned signal then triggers the multivibrator circuit 74 to send a clean zero volts square wave 90, shown in (e), o a normal +5 volts signal 92. The sensor module 10 (FIG. 1) is supplied directly from the battery source. There is a +5 volts voltage regulator in the sensor module 10 that supplies the module integrated circuits.

Monitor module 100 (FIG. 6) has four component features: module connection ports and control switches, heart beat counter, microprocessor board and alert module electronics. The monitor module 100 has three connection ports 102 and five switches, 3 external switches 104 and 2 internal switches 106. The three modular phone jacks 102 are used for connecting the sensor and alert modules 10 and 200 to the monitor module 104 and for providing a communications port. In addition, there is an auxiliary battery connection port 107.

Figure 6:
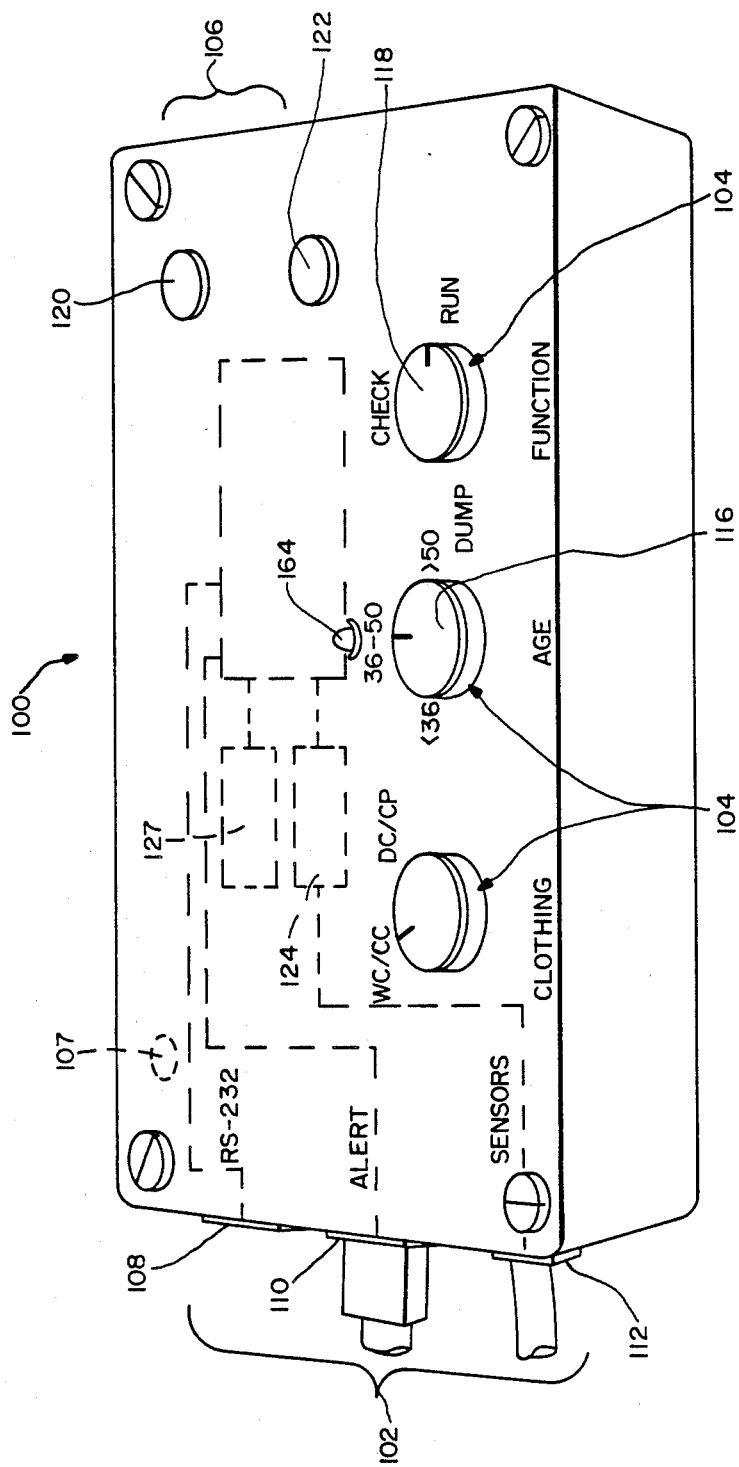
FIG. 6 is a perspective view of a second portion of the personal monitor of FIGS. 1-4.

Communication port 108 is the top plug in FIG. 6, which is labeled RS232. It is an RS232C port requiring a six wire phone plug attached to the special communications cable supplied with an Onset Computer datalogger. This connection is necessary for communication with the microprocessor for (1) monitoring PM performance during laboratory tests and demonstrations, (2) calibration check of the PM, (3) obtaining PM data using the DUMP function, and (4) communicating with the microprocessor for program check-out or modification.

Alert module port 110 is the middle port, labeled Alert. It is an eight connector jack to attach the alert module.

Sensor module port 112 is the bottom phone jack. It has four leads that attach to the sensor module 10.

Auxiliary battery port 107 is located on the top side of the monitor module 100. It allows for the connection of a second or alternate battery to power the monitor module. It can also be used to extend the service time of the PM.

The external switches 104 are located on the front surface of the monitor module. Clothing switch 114 is a two-position switch to select and indicate clothing ensemble: (1) work clothes or single cotton coveralls and (2) double cotton coveralls or impermeable (vapor barrier) clothing. Age switch 116 is a three-position switch used to indicate which set of MTA thresholds should be used. The three age groups are: (1) less than 36 years; (2) 36–50 years; and (3) greater than 50 years. Function switch 118 indicates the mode of operation for the PM. The details on mode are discussed in the section on Software below. The modes are: (1) DUMP mode; (2) CHECK which allows for a system checkout and calibration; and (3) RUN mode.

There are two internal switches 106, which can be accessed through taps in the front cover. DEMO/DUMP format switch 120 is an internal three-position switch located in the upper right corner of the module as shown. It serves two purposes. In the CCW position, all of the data stored during the use of the PM is sent to the communications port 108 during the DUMP routine (see Software). In the middle position, the MTA data are deleted from the dump output. In the CW position, two actions are possible. In DUMP, the MTA data are deleted from he dump output. In the RUN mode, program control passes over to an alert demonstration routine. This switch can be changed through the upper tap in the cover.

Baud rate switch 122 is located near the right side of the module 100 and in the middle as shown. It selects the communications port speed for data transmission: (1) 300 baud, (2) 1200 baud and (3) 9600 baud. If the terminal (printer, computer, etc.) does not support the XON/XOFF communications protocol, it is best to communicate at 300 baud. At the higher baud rates, output data (especially during the DUMP routine) may become garbled or lost. Communications specifications include 8 bit words with one stop bit and no parity check. This switch can be changed through the lower tap in the front cover. The baud rate is changed to the new value at powerup or after an entry into the DUMP mode (see Software).

Heart beat counter 124 is a typical integrated circuit with a trigger (called a clock) input, a reset control, and 12 output bits. The counter 124 will count each heart beat as sent from the sensor module 10 into the trigger input. This counter is reset to zero when a positive pulse is sent to the reset input. Only the first seven bits of the counter are used as input to microprocessor board 126. This means that values from 0 to 127 can be read by the counter 124. If the counter tries to go to 128 before a reset, it will roll over to zero and begin again. The counter 124 is read and reset every 30 seconds, which means that a heart rate up to 254 beats per minute can be counted, which is higher than is physiologically possible. The counter 124 is reset by the microprocessor 126 under the program control.

The microprocessor board 126 is a commercially available Tattletale Model II datalogger designed for OEM applications by Onset Computer. It uses a customized version of BASIC (TTBASIC, Version 1.72). The manual for this board describes the hardware and programming language. The important features of the microprocessor hardware are summarized below.

The datalogger hardware is contained on a 7.4 cm by 12.7 cm (3×5 in.) printed circuit board. The hardware includes an 8 bit microprocessor 126 with a 32K EEPROM (electrically erasable programmable read only memory), 256K of dynamic RAM 127, 8 channel 8 bit analog-to-digital (A/D) converter, and a 14 pin digital I/O (14 bits of digital input and/or output). In addition there is an RS232C serial communications port. There are 21 locations to store numbers in nonvolatile memory (EEPROM) accessible from TTBASIC. When the processor is powered up (turned on), it loads the program stored in EEPROM into RAM 127 and begins execution of the program. Under the PM application, the ROM contains the TTBASIC interpreter and the PM software written in TTBASIC. The PM software and the TTBASIC reserved variables actually occupy about 60K of RAM, leaving the balance for storage of PM data collected during operation. During each minute of operation, the PM stores about 22 bytes of data or about 1.2K per hour. While the data storage was designed for laboratory and field trial tests, it may have applications for routine evaluation of individual stress and job demands in a broader heat stress management program.

Figure 7:
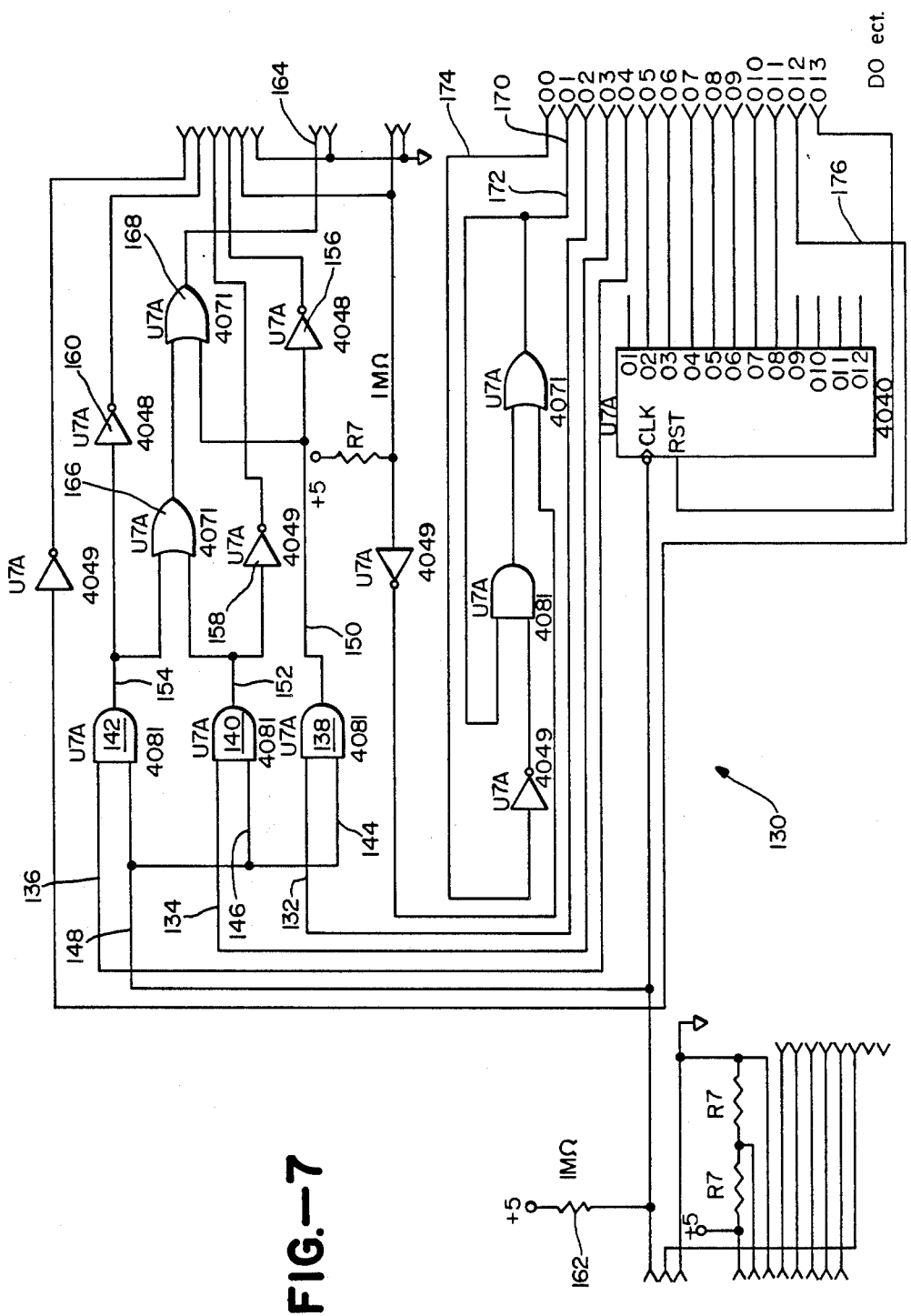
FIG. 7 is a schematic diagram of a third electrical circuit used in the second portion of the personal monitor shown in FIG. 6.

FIG. 7 shows a circuit diagram for the alert module electronics 130, which are contained in the monitor module 100. The digital lines 132, 134 and 136 for the green, yellow and red LEDs are brought out to separate AND gates 138, 140 and 142. On the second legs 144, 146 and 148 of each AND gate 138–142 is the heart beat signal from the sensor module 10. The AND gate 138–142 outputs 150, 152 and 154 then go through a separate amplifier 156, 158 or 160 to drive their respective LEDs. When the program calls for an LED to be on, it will be on and flash off with each heart beat. (Remember that the heart beat line is at +5 volts except when a QRS wave is detected.) It should be noted that if the sensor module 10 is not attached, a pullup resistor 162 will keep the heart beat signal high. The circuit provides for a monitor module LED at 164 that also flashes with heart beat when any one or more of the alert module LEDs is turned on The outputs 150–154 are connected to the monitor LED output 164 through OR gates 166 and 168 as shown.

When command button line 170 is activated, logic line 172 supplying channel 1 of the digital I/O will be taken high (+5 volts). This line will remain high until a reset high signal (+5 volts) is sent out to line 174 on channel 0 of the digital I/O by the PM program.

Figure 8:
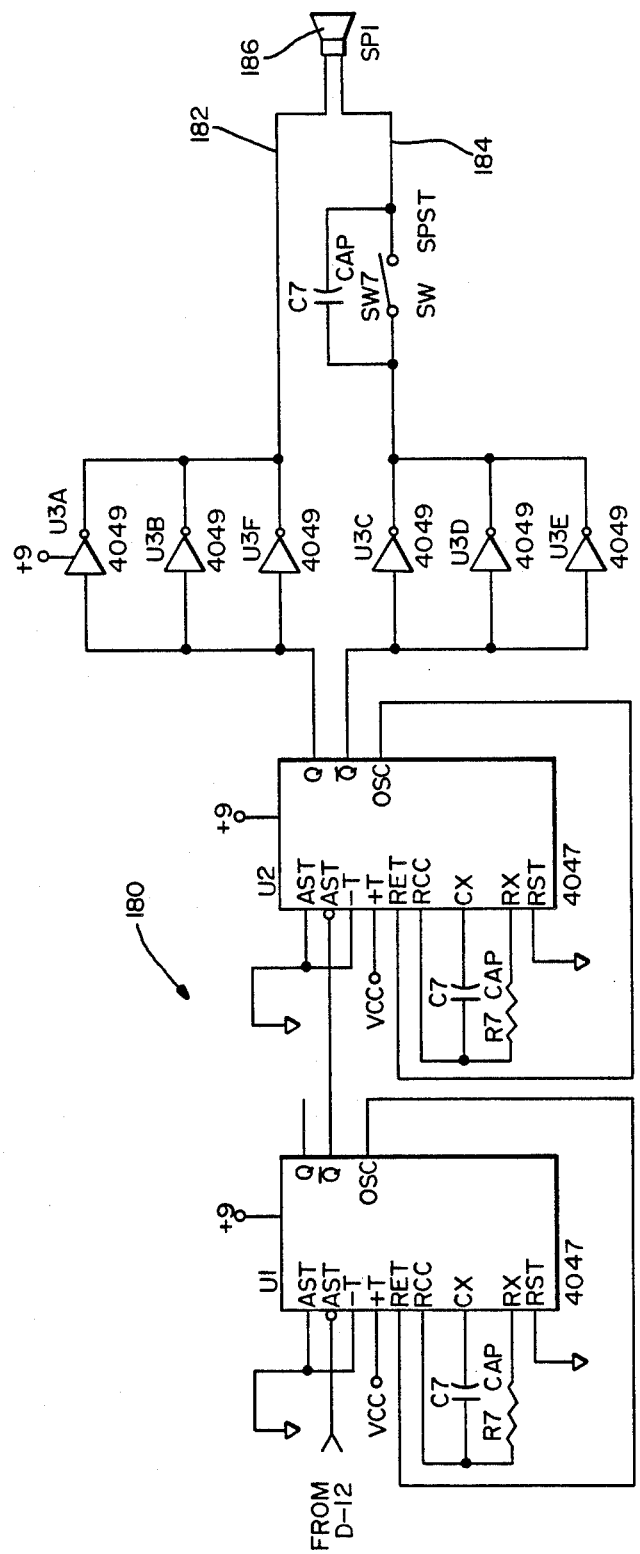
FIG. 8 is a schematic diagram of a fourth electrical circuit used in the second portion of the personal monitor shown in FIG. 6.

When an aural alarm is requested by the PM program, digital I/O channel 12 on line 176 will go to zero volts briefly which triggers a timer 180 (FIG. 8). The timer 180 allows a tone to sound for 3 seconds. The sound is generated by alternating plus and minus legs 182 and 184 of a battery on the piezoelectric drive of a diaphragm 186 of the alert module (see also FIG. 9).

The monitor module has the LED 164 provided on the front of the module. This LED 164 is activated at the same time one or more of the LEDs 208–212 (FIG. 9) on the alert module 200 is called. The primary purpose is to verify a good heart beat tracking without looking at the alert module. There may be some applications when the PM is used to gather physiological data and the alert module is not connected. When a battery is connected directly through the auxiliary battery jack 107 of the monitor module 100, the alert module 200 is not needed to power the PM (see alert module in the following section). The auxiliary jack 107 can also be used to prolong the PM power supply or to preserve data collected after the alert module is disconnected. (All information from a PM session is lost if power to the microprocessor 126 is interrupted.)

Figure 9:
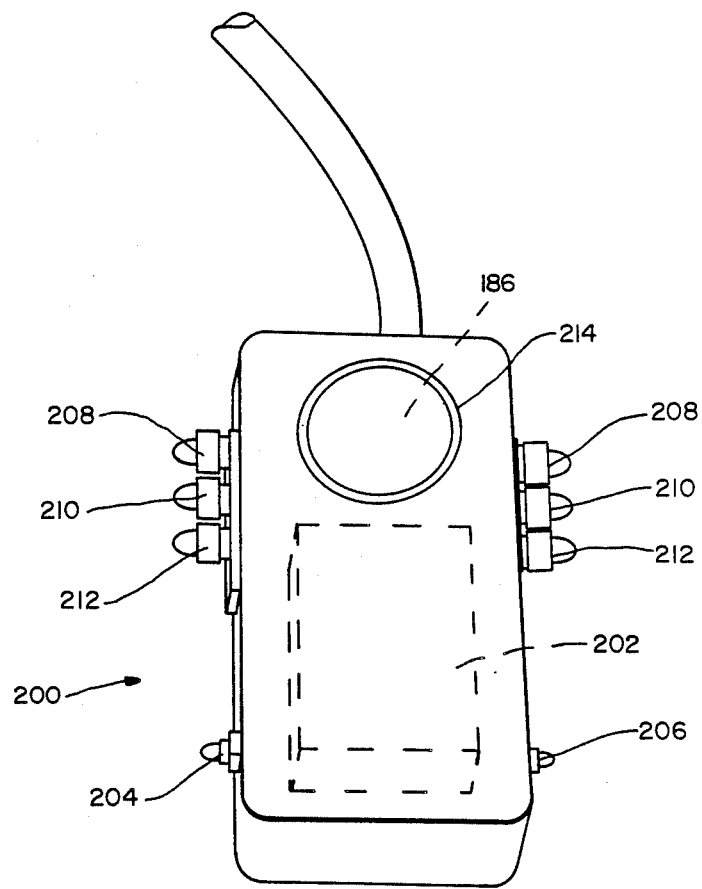
FIG. 9 is a perspective view of a third portion of the personal monitor of FIGS. 1-4 and 6-8.

Alert module 200 is shown in FIG. 9. It has four components: battery, command buttons, alert LEDs and tone generator. The alert module 200 carries a 9-volt transistor battery 202, which is the principal power supply for the PM. Battery voltage is checked by the software. Two buttons 204 and 206 are placed on opposite sides of the alert module 200. If both buttons are pressed simultaneously, the command logic signal on line 174 (FIG. 7) is set High (+5). The PM program makes use of this signal to take special actions determined by the function switch 118 (FIG. 6) position. Two sets of three alert LEDs 208, 210 and 212 are available, one set on each side of the module 200. From top to bottom, they are red, yellow and green. Which pairs flash with heart beats is under program control through the monitor module 100. A piezoelectric driven diaphragm 186 is inside the module 200, with an opening 214 to the outside. This provides the actual aural alarm at the command of the microprocessor 126 and is driven by electronics in the monitor module 100.

Software

The personal monitor uses an algorithm to assist an individual in determining exposure to heat stress. The algorithm is incorporated into a program to control data collection of disk 14 (FIG. 1) temperature and heart rate, manipulate the data as necessary to obtain relevant information, and activate appropriate alerts. The program reflects the implementation of the algorithm within the prototype hardware framework. The following description of the PM software describes the critical measures and the decision-making structure.

The PM hardware described above is responsible for monitoring insulated skin (disk) temperature and heart beats (stored in a counter) and for providing the alert status and user control. The program, stored in an EEPROM (electrically erasable programmable read only memory) controls the datalogger microprocessor 126 (FIG. 6).

The following list is the description of the critical variables for the PM as they are used in the algorithm.

| | |
|---|---|
| $T_d$ | Skin temperature taken at one minute intervals |
| HR | Heart beats counted over the 30 seconds, multiplied by 2 for rate |
| MTAn | Moving-time-average (MTA) HRs over past n-minutes (n=5, 10, 20, 30, 45, 60, 90) (initially set to 75 and updated by HR every minute) |
| Green | Alert that indicates Acceptable (normal) physiological stress |
| Yellow | Alert that indicates a Warning level |
| Red | Alert that indicates an Action level |

Figure 10:
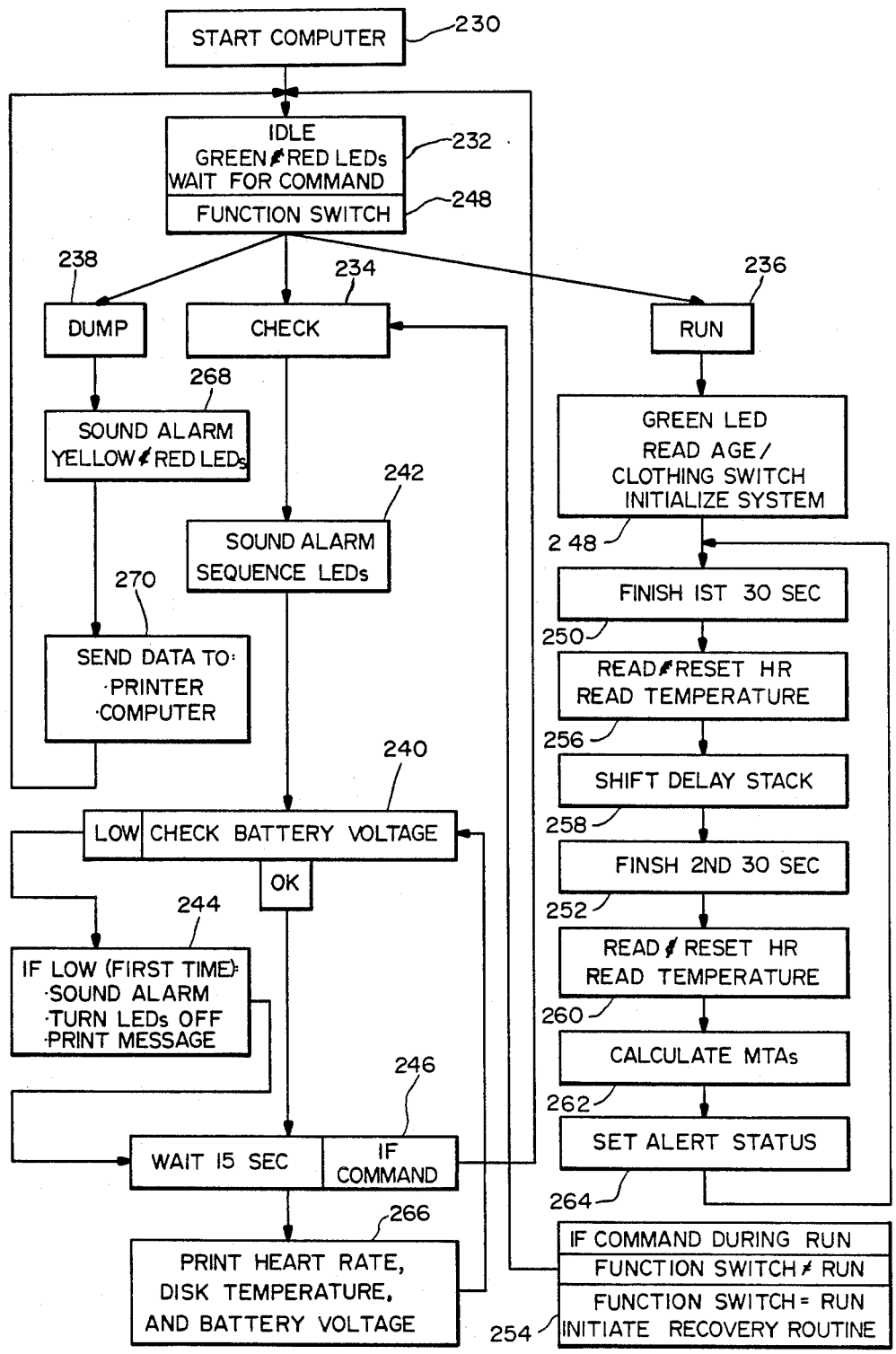
FIG. 10 is a flow chart useful for understanding operation of software forming a part of the invention.

An overview of the program control process is shown in FIG. 10. A hardware allocation, variable assignments and listing of the program that embodies the PM algorithm is attached as an appendix to this specification.

PM Modes and Routines

When the alert module 200 (FIG. 9) is plugged into the monitor module 100 (FIG. 6) (or when an auxiliary battery is attached), the microprocessor 126 is activated at 230. Its first step 232 is to load special factors from nonvolatile memory and turn on Green and Red LEDs 212 and 208. The LEDS will flash with heart beats if the system is receiving an EKG signal. The monitor (or computer) is in the IDLE mode waiting for the command buttons 204 and 206. After reading the function switch 118, the PM enters one of three modes 234, 236 or 238:

CHECK, which also allows a calibration check

RUN, which starts the PM to monitor physiological state and to control the alerts DUMP, which allows the time course of the user's physiological state and the PM's alert information to be downloaded to a printer or another computer for inspection Line numbers of the program code are given in the following discussion to link the discussion to the program. If the communications port 108 is used to connect the PM to a terminal, PM activity messages can be monitored.

The CHECK mode 234 (lines 150 to 330) actually serves two functions: system check prior to using the PM and calibration check. Both functions operate together and appear the same to the ordinary user. The first action 240 is to test the battery voltage. If the voltage is too low, an alarm is given and all LEDs are turned off at 244. If the voltage is good enough for 4 hours of operation, the program will test the diaphragm sound transducer 186 and the LEDs 164, 208, 210, 212 at 242 by sounding an alarm and turning on each LED on in sequence at one second intervals. This allows for a visual check of the LEDs and an aural check of the alarm.

The LEDs 164 and 208–212 will flash with each heart beat if the sensor module 10 is connected and a good EKG signal is being obtained. If the sensor module 10 is disconnected, the lights will remain steady. If the EKG signal is poor, either the LEDs will not flash or the flashing will be very irregular (not a rhythmic beat like the heart). While in CHECK, the LEDs will continue to light in sequence and the battery will be checked every 15 seconds until the command buttons 204 and 206 are actuated at 246, at which time the program returns to the IDLE mode 232 It then waits to read the function switch 118 at 248 with the next activation of Command If the battery voltage drops below the starting level criterion, the alarm sounds and all LEDs go off.

While in the CHECK mode 234, a calibration check can be made This would be a bench test during which a printer or computer terminal is connected to the PM through the RS232 port 108 The temperature sensor 14 is placed in a stirred water bath that is between 35° and 40° C. (95° and 104° F.) and measured with a thermometer with an accuracy of ±0.05° C.(0.1° F.) A pulse generator is attached through a voltage divider to the electrode clips 12 so that a 2 millivolt pulse (positive to the left electrode) is delivered. Every 15 seconds, pulse rate in pulses per minute, disk temperature in degrees-C times 10 (e.g , 375 means 37.5° C.) and battery voltages times 10 (e.g., 77 means 7.7 volts) are sent out on the RS232 port 108 If the temperature readings are within 0.05° C. and the pulse rate within 2 pulses per minute, the sensor module 10 and monitor module 100 are working correctly. The calibration check can proceed if the low battery signal is given, but erroneous temperature readings may occur if battery voltage is less than 7.1 volts. The calibration check is ended by pushing the command buttons 204 and 206, which returns the program to the IDLE mode 232.

When the function switch 118 reads RUN at the Command, the PM enters the operations mode (lines 1000–1800) At this point, only the Green LEDs 212 are on, and Yellow and Red are deactivated In this mode, the PM monitors physiological state There are four main activities in the RUN mode: initialization 248, after first 30 seconds of each minute 250, after second 30 seconds of each minute 252 and recovery heart rate routine 254. Initialization 248 is the first activity, and is performed only when entering the RUN mode 236 (lines 1000–1120) from the IDLE mode 232. The Age and Clothing switches are read. Depending on switch positions, the relevant thresholds for Green-to-Yellow (Warning), Yellow-to Green (Reset), and Yellow-to-Red (Action) for disk temperature and moving-time-average heart rates (MTAs) are loaded into the array. All heart rate values in the delay stack and the MTAs are set to 75, the assumed value for resting HR. The timer and heart beat counter are set to zero.

At the end of the first half of every minute following the start in RUN mode (lines 1150–1290), the battery voltage and heart rate counter are read at 256. The counter is immediately reset to zero, and the heart beats are doubled to give the rate in beats per minute (bpm) (subroutine 10000). The next step is to perform a quality check on the heart rate (subroutine 10400). If the value is between 40 and 220 bpm and the increase from the previous reading is less than 30%, the heart rate is recorded as read. If HR<40 or HR>220, then the value is out of acceptable bounds. This means the rate is physiologically too high or too low and is due to a poor EKG signal. In either case, HR is taken as the preceding recorded value (the one taken from 60-30 seconds preceding the current time). An increase greater than 30% is not likely and may be due to some spurious pulses from the EKG electrodes. In this case, the increase is limited to 30%. This will not have any real effect on the MTA's if it is a true increase because HR will be quick to reach the new value. If the increase is artificial, HR returns to the correct value and the effect of the increased value is contained, for a small effect on the MTAs.

A variable called the net number variable (HR error index) is increased by one for each questionable reading and reduced by one for each good reading, but s not allowed to go less than zero or more than 7. If there are a net number of 7 questionable readings, where the 30 second HR values were adjusted, an alarm is given. In the worst case, this means there are 3 complete minutes of questionable data for HR. The alert for inaccurate HR data is the aural alarm and all LEDs turning on.

The next step is to shift the delay stack by one minute at 258. The delay stack is illustrated in FIG. 11. The first value is for the current minute, the second for the preceding minute, third for two minutes preceding, and so on until the last value represents the 90th preceding current time. Remember that a resting value of 75 is assumed at the start, and therefore the stack is prefilled with 75s. The stack is shifted so that, first the value in 89 replaces 90, then 88 replaces 89, and so on until the last current value at 0 is moved to 1. The stack represents the time course of HR for the past 90 minutes, with the 91st minute thrown away. At this point, the rate for the first half minute is placed at 0. The program now checks to see if a recovery is in progress. This is discussed below.

The battery voltage is checked. If it is less than or equal to 7.0 volts for three consecutive readings, an alarm is sounded and all LEDs are cleared (turned off). The poor HR alert overrides. The device continues to operate so that data is collected, but there will not be a continuous display of alert status. At this point, the temperature readings may not be accurate, but the failure mode is toward increasing values so it is protective.

In the same manner as described above, the heart rate counter is read and reset at 260, and a quality check on HR is made. (Lines 1300–1800) The HR value for the second 30 seconds is averaged with the value for the first 30 seconds, which gives the total count for the past minute. This value is placed in location 0 of FIG. 11. The next step is to calculate the MTAs at 262. MTA-5 is the moving-time-average for 5 minutes, and would be the sum of values from 0 to 4 in FIG. 11 divided by 5.

MTA-10 would be the sum of values 0 to 9 divided by 10. As a computational shortcut, the sums are maintained in separate variables, the newest value (always location 0 is added to the total) and the oldest value is subtracted. For MTA-5, the oldest value would be at location 5; for MTA-10 at 10, and so on. Once the MTAs have been updated, the alert status can be determined at 264. The physiological state is represented by the values D1 through D8 in FIG. 12. The respective threshold values are represented in similar fashion with W being the Warning (Yellow) level, R being the Reset (return to Green) level and A being the Action (Red) level.

The following decision process is used in the program:

1. If YELLOW is current alert state, should PM be set to GREEN?
    *for m=1 to 8: if $D_m < R_m$ then $WF_m = 0$
    ($WF_m$ is a flag to indicate a change to GREEN)
    *WFT=$\Sigma WF_m$: if WFT=0 then set GREEN
2. If YELLOW is current alert state, should PM be set to RED?
    * for m=1 to 8: if $D_m > A_m$ then set RED
3. If GREEN is current alert state, should PM be set to YELLOW?
    *for m=1 to 8: if $D_m > W_m$, then $WF_m = 1$ ($WF_m$ is a flag to indicate a change to YELLOW)
    *WFT=$\Sigma WF_m$: if WFT>0 then set alert state to YELLOW
4. Wait to next minute: collect new data and go to 1

If there was a change in alert status due to YELLOW to GREEN, YELLOW to RED, GREEN to YELLOW, an alarm sound is given (steady tone for 3 seconds) and the appropriate LED is selected. This will occur even if the battery is too low for continuous operation. In this case, the LED will stay on for 30 seconds. The physiological data and PM status for the preceding minute are stored in the memory. These data can be retrieved in the DUMP mode 238 (see below). If the PM device is attached to a printer or terminal (unlikely for field use), a printout is provided for every minute of the time, current HR, disk temperature ($\times 10$), alert status and LED status (0-all LEDs off, 1-GREEN, 2-YELLOW, 3-RED, 4-all LEDs on), heart rate quality status and battery voltage ($\times 10$) at 266. This feature is provided for laboratory tests and demonstrations. The program then returns to wait until the first 30 seconds of the next minute are complete.

The recovery routine 254 (subroutine 10600) can be invoked at any time during the RUN mode by activating the command buttons 204 and 206 (subroutine 10700). When the Command is requested, the function switch 118 is checked. If the selected function is RUN, then recovery routine 254 is requested. If a second request is made before the first is serviced, then the first one is ignored and recovery is reinitialized. The first step is to synchronize the request to the sampling period by moving it to the nearest one-half minute on the PM clock. By doing this, the calculation of $P_1$, $P_2$, and $P_3$ (see Section 2) is off by $\pm 15$ seconds in the worst case.

The recovery routine follows these steps:
1. Record heart beats for the following intervals:
    *30 to 60 sec. after request ($P_1$=total beats $\times 2$)
    *90 to 120 sec. after request ($P_2$=total beats $\times 2$)
    *150 to 180 sec. after request ($P_3$=total beats $\times 2$)
2. If $P_3 < 90$ then
    *sound alarm
    *flash GREEN
    *go to 5
3. If $P_3 < 120$ and $(P_1 - P_3) > 10$ then
    *sound alarm
    *flash YELLOW for 15 seconds
    *go to 5
4. Sound alarm and flash RED for 15 seconds
5. Return LEDs to previous status and leave recovery routine The values for $P_1$, $P_2$, and $P_3$ are taken at one minute intervals and represent 30 second counts for the second half of the three recovery minutes, as called for by the procedure. When all three values have been obtained, the recovery status is presented to the user. First, the aural alert is sounded, then the appropriate LED is flashed on for 1 second and off for 1 second for 15 seconds. The LEDs are then returned to their previous state. The result of the recovery routine is sent out on the RS232 port 108 and stored in the DUMP memory.

The RUN mode can be terminated by changing the function switch from RUN to either CHECK or DUMP and pushing the command buttons 204 and 206. Program control will always go to the CHECK mode. If the RUN mode is entered with the Demo/Dump Format switch in the CW position, a demonstration of the PM alerts is given. In 5-second intervals the PM will go through the following alert sequence: Green-Yellow-Green-Yellow-Red. At the Red LED, the program waits ten seconds for the command buttons 204 and 206 to demonstrate a Yellow recovery alert. The PM will return to the IDLE mode if the command buttons 204 and 206 are activated with a Green or Yellow LED on or 10 seconds after the Red recovery alert.

The DUMP mode 238 (beginning at line 15000) permits the extraction of information on both physiological and PM performance at the end of a PM session. To preserve the stored data, the user must
1. Select CHECK or DUMP on the function switch 118 to exit RUN
2. Activate the command buttons 204 and 206
3. Attach auxiliary battery or do not disconnect Alert module
4. Remove Monitor module from person
5. Connect a printer or computer terminal to the RS232 port 108
6. Select DUMP on the function switch 118
7. Activate the command buttons 204 and 206

The aural alarm is given and the LEDs go to the Yellow and Red on (Green off). The data will be sent at 270 in the selected format, at the selected baud rate, 8 bits/word, 1 stop bit, and no parity. If the receiving unit does not support the XON/XOFF protocol, the results may become garbled due to buffer overflow.

The baud rate on the communications port can be changed using the Baud Rate switch. The change becomes effective immediately upon entering the DUMP mode. The Demo/Dump Format switch is also read and acted on when the DUMP mode is entered.

There are basically two data types. One is the principal data that are stored at one minute intervals. These include the seven MTAs, so that the calculated averages (values used to determine alert status) are available. (The MTA output can be omitted as an option selected with Demo/Dump Format switch.) Flag Status is an eight digit number where each digit represents a working variable (disk temperature and MTAs) that indicates individual alert levels. HR error index is the net number of questionable 30 second heard rate values (labelled QC for quality check. The last entry is battery voltage times 10. The second type of output is recovery data, which gives the report time, recovery status, and the three recovery heart rates.

The program will automatically return to the IDLE mode 232 at the end of the download. The download can also be stopped by activating the command buttons 204 and 206, which returns the program to the IDLE mode.

Four special purpose routines were written into the PM program to aid development. They are stored at the end. To use these routines, the program must be interrupted by sending (entering or typing) from a terminal a control-A(_A) in the IDLE mode. At this point control passes to TTBASIC monitor.

Disk temperature calibration factors, starting battery voltage criterion and serial number can be changed by executing "GO TO 21000." The routine will ask for the intercept (°C.) and then the slope (°C./unit), each times 1000. It then asks for the battery voltage times 10 that is the minimum required for PM operations. These values are then stored in nonvolatile memory and printed out for verification.

Run counter and serial number can be reset to a new number by executing a "GO TO 21100." A deep sleep routine at line 30000 was used to conserve battery life without removing power to the PM. It is useful for the long term storage of PM data. A/D converter readings for all 8 channels and battery voltage are provided by starting execution at line 31000. It updates at 3 second intervals. Control can be returned to the PM by either removing power and restarting, or by executing a "RUN."

It should now be readily apparent to those skilled in the art that a novel personal monitor and process for heat and work stress has been provided. There are three novel features: First, a novel temperature sensor especially adapted for use in the monitor and process capable of achieving the stated objects of the invention has been provided. Second, the process uses multiple moving averages in time to examine heart rate patterns. Thresholds for each of the multiple moving time averages are used to mark the point of excessive physiological demand. Third, a commonly accepted heart rate recovery routine has been automated within the PM. The personal monitor and process measures physiological responses to work and heat stress and provides recommendations to the user in an industrial environment which will allow the user to limit his or her exposure to the physiological stress in an informed manner. The monitor and process neither provides the user with a multitude of inappropriate warnings nor allows the user to exceed safe limits without providing appropriate warnings. The novel temperature sensor monitors of core body temperature in a consistent and reliable manner.

It should further be apparent to those skilled in the art that various modifications in form and details of the invention as shown and described may be made. For example, while the hardware has been implemented with commercially available standard integrated circuits in three modules, it could be made substantially smaller through the use of custom integrated circuits, resulting in one or two smaller modules. An infrared or radio transmission link could be used between the modules and/or sensors. With such links, the system could also telemeter out to a supervisory unit. The switches could be replaced with a different user interface. The sensor electrodes could be implemented as a two electrode system, rather than a three electrode system by providing a single EKG active electrode and using the temperature sensor electrode as the EKG passive electrode as well. The system can be used for other applications, such as for sports and/or rehabilitation training, and as a physiological data logger. For the sports and rehabilitation application, the system could be modified to provide a programmed training regimen that varies in time and provides both a minimum and maximum alert, so that the user obtains a desired level and pacing of exercise, without exceeding safe limits. While the temperature sensor is shown as particularly configured for monitoring core body temperature, it could be adapted for monitoring the temperature of a wide variety of other objects as well. It is intended that such changes be included within the spirit and scope of the claims appended hereto.

APPENDIX TO BERNARD ET AL APPLICATION

FILE A-46115/AJT/WEH

HARDWARE ALLOCATION
Prototype PM Series 100

Analog-to-Digital Converter

Channel

0      Age Switch*
            High: >50 years
            Middle: 36-50 years
            Low: <36 years 1    Clothing Switch*
       High: Plastics / Double Cottons
       Low: Work Clothes / Cotton Coveralls 2    Function Switch*
       High: RUN
       Middle: CHECK
       Low: DUMP 3    Demo/Dump Format Switch*
       High: Alert demonstration in RUN and skip MTAs in DUMP output
       Middle: Skip MTAs in DUMP output
       Low: Normal output 4    Baud Rate Switch*
       High: 9600
       Middle: 1200
       Low: 300

5    Disk Temperature (36.4°C = 0 and 0.025°C/unit)

6    Battery voltage (factory)

7    Board temperature (factory) – not used in PM application

* Nominal values: High = 5 volts (255 units); Middle = 2.5 volts (128 units); Low = Ground (0 units)

Digital I/O

Channel

0    Command Reset - output

1    Command Button - input

LEDs - output
2    Green
3    Yellow
4    Red

Heart Rate Counter (7 bits) - input
5    Least Significant Bit
6
7
8
9
10
11   Highest Order Bit 12   Audio Alarm Activation (set to switch off / clear to switch on) - output 13   Heart Rate Counter Reset - output

ALLOCATION OF VARIABLES
Software version 3.1

| | |
|---|---|
| A | Temporary |
| B | Temporary |
| C | Temporary |
| D | Temporary |
| E | Temporary |
| F | Preceeding HR |
| G | HR Error Index |
| H | HR for current 30 sec |
| I | Idle Period |
| J | Battery Voltage (x10) |
| K | Idle Time Hold |
| L | Not Used |
| M | Not Used |
| N | Not Used |
| O | Not Used |
| P | Recovery Index (pointer/status) |
| Q | Recovery Flag (related to T) |
| R | Low Battery Voltage - intermediate counter |
| S | LED Status (0=all LEDs off; 1=GREEN; 2=YELLOW; 3=RED; 4=all LEDs on) |
| T | Time (Number of 30s intervals) |
| U | Disk Temperature x10 (°C) |
| V | Temporary Hold for W |
| W | Alert Status (1=Acceptable/GREEN; 2=Warning/YELLOW; 3=Action/RED) |
| X | =1: Skip MTAs in Dump Output |
| Y | Highest Value of Z |
| Z | Data Storage Pointer |

LOCATIONS IN ARRAY (@) OF PROGRAM VARIABLES
Software version 3.1

Array Element

Locations available for EEPROM storage via VSTORE and VGET

| | |
|---|---|
| 0 | Intercept (x1000) of Disk Temperature Sensor Calibration Line |
| 1 | Slope (x1000) of Disk Temperature Sensor Calibration Line |
| 2 | Starting Battery Voltage Criterion |
| 3 | Serial Number of PM |
| 4 | Run Number (number of times PM was in RUN for more than 9.5 min) |
| 5-19 | Not Used |

Thresholds for Warning (GREEN to YELLOW)

| | |
|---|---|
| 20 | Disk Temperature |
| 21 | MTA-5 |
| 22 | MTA-10 |
| 23 | MTA-20 |
| 24 | MTA-30 |
| 25 | MTA-45 |
| 26 | MTA-60 |
| 27 | MTA-90 |

Thresholds for Reset (YELLOW to GREEN)

28  Disk Temperature
29  MTA-5
30  MTA-10
31  MTA-20
32  MTA-30
33  MTA-45
34  MTA-60
35  MTA-90

Thresholds for Action (YELLOW to RED)

36  Disk Temperature
37  MTA-5
38  MTA-10
39  MTA-20
40  MTA-30
41  MTA-45
42  MTA-60
43  MTA-90

Current Values

44  Disk Temperature
45  MTA-5
46  MTA-10
47  MTA-20
48  MTA-30
49  MTA-45
50  MTA-60
51  MTA-90

Alert Flag Status: 0=Acceptable/GREEN; 1=Warning/YELLOW; 2=Action/RED

52  Disk Temperature
53  MTA-5
54  MTA-10
55  MTA-20
56  MTA-30
57  MTA-45
58  MTA-60
59  MTA-90

60  G: HR Quality Flag (net variable between 0 and 7)

Totals (sums of HR counts)

61  MTA-5
62  MTA-10
63  MTA-20
64  MTA-30

| | |
|---|---|
| 65 | MTA-45 |
| 66 | MTA-60 |
| 67 | MTA-90 |
| 68-69 | Not Used |

Heart Rate Delay Stack

| | |
|---|---|
| 70 | HR for 1st 30 sec |
| 71 to 161 | Past Heart Rates in 1 minute intervals |

Recovery Heart Rates

| | |
|---|---|
| 162 | $P_1$ |
| 163 | $P_2$ |
| 164 | $P_3$ |

```
10 REM ******** PERSONAL MONITOR PROGRAM *********
20 REM COPYRIGHT (C) 1987 ELECTRIC POWER RESEARCH INSTITUTE, INC
25 REM ALL RIGHTS RESERVED
30 REM VERSION 3.1, 3/30/87
40 REM WESTINGHOUSE R&D AND PSU - RP2705-5
50 REM WRITTEN IN TTBASIC FOR PROTOTYPE PM HARDWARE USING
60 REM ONSET COMPUTER'S TATTLETALE DATA LOGGER (MODEL II, REV 1.72)
65 PCLR0,3,13: PSET2,4,12: Y=6: REM INITIALIZE
70 SLEEP0: SLEEP200:  REM ALLOW PM TO POWER-UP
75 XSHAKE 500: REM SET XON/XOFF W/ 5 SEC TIMEOUT
80 REM GET TEMP INTRCPT/SLOPE, START BAT VLT, S/N, RUN NMBR
85 VGET @(0): VGET @(1): VGET @(2): VGET @(3): VGET @(4)
90 DIM(165): GOSUB 15500: REM SET BAUD RATE, PRINT HEADER
100 PCLR0,3,13: PSET2,4,12: REM CLR RESETS - SET GRN & RED LEDS
104 PRINT: PRINT 'IDLE'
105 SLEEP100 GOTO 110: REM WAIT FOR INTRPT W/CMND(=COMMAND BUTTON)
106 GOSUB 15400: REM ^A STOPS PRGM (R&D ONLY)
107 GOTO 105
110 GOSUB10100: REM ACKNOWLEDGE CMND
120 A=CHAN(2): REM GET FUNCTION
130 IF A<64 GOTO15000: REM DUMP ROUTINE (RTRN TO 100)
140 IF A>192 GOTO 1000: REM START MONITORING ROUTINE
150 REM    *** CHECKOUT/CALIBRATE LOOP ***
151 REM ALARM SOUNDS ONCE AT START AND IF BATTERY IS LOW
152 REM LEDS ROTATE ON AT 1 SEC INTERVALS (GRN-YEL-RED)
154 REM PRINT HR, DISK TEMP, AND BATTERY LEVEL EVERY 15 SEC
155 REM IF LOW BATTERY, ALL LEDS OFF
156 REM RTRN TO IDLE W/ CMND
160 GOSUB 10200: PSET2: PCLR3,4: REM ALARM & START WITH GRN
165 B=1: ?=0
169 PRINT: PRINT 'SYSTEM CHECK': PRINT
170 PRINT '     HR    TEMP    BAT': PRINT '    bpm    Cx10    Vx10'
180 SLEEP0: PSET13: PCLR13: REM CLEAR HEART CNTR
190 J=BAT: REM GET BATTERY VOLTAGE
200 IF J>=@(2) GOTO 210
201 PCLR2,3,4: REM LOW BATTERY - TURN OFF LEDS
202 IF B=2 GOTO 210: REM ALARM & PRINT NOTICE 1ST TIME
```

```
203 IF ?>1000 GOSUB10200: REM BAT OK ON 1ST PASS
204 PRINT 'BATTERY IS TOO LOW FOR EXTENDED USE! V=',J,' (<',@(2),')'
205 B=2
210 E=1: REM LOOPS THROUGH THIS 3 SEC SECTION 5 TIMES
220 SLEEP100 GOSUB 10100: GOTO100: REM WAIT 1 SEC
230 IF B=1 PCLR2: PSET3: REM YEL ONLY UNLESS LOW BAT
240 SLEEP100 GOSUB 10100: GOTO100
250 IF B=1 PCLR3: PSET4: REM RED ONLY UNLESS LOW BAT
260 SLEEP100 GOSUB 10100: GOTO100
270 IF B=1 PCLR4: PSET2: REM GRN ONLY UNLESS LOW BAT
275 E=E+1: IF E<6 GOTO220
280 J=BAT: REM GET BATTERY VOLTS
300 GOSUB 10800: REM GET DISK TEMP
310 GOSUB10000: H=H*2: REM GET HR (x2 FOR 15 SEC BASE)
320 PRINT #7, H, U, J: REM HR W/ BAT & TEMP x10
330 GOTO 200
1000 REM ***** MONITORING ROUTINE (RUN MODE) *****
1001 PCLR3,4: PSET2: REM SET GRN LED
1002 A=CHAN(3): IF A>196 GOTO32000: REM ALERT DEMONSTRATION
1004 PRINT: PRINT 'RUN': PRINT
1005 SLEEP0: PSET 13: I=1: GOSUB10300: PCLR13: REM CLR TIMER/CNTR
1010 ?=0: REM RESET TIMER VARIABLE -- RESET EVERY 30 SEC
1020 Z=0: A=CHAN(0): REM SELECT MTA CRITERIA
1021 IF A<64 GOTO1040: REM <36
1022 IF A>192 GOTO1050: REM >50
1029 REM 36-50
1030 @(21)=152: @(22)=147: @(23)=142
1031 @(24)=139: @(25)=132: @(26)=131
1032 @(27)=129: @(29)=150: @(30)=145
1033 @(31)=140: @(32)=137: @(33)=130
1034 @(34)=129: @(35)=128: @(37)=157
1035 @(38)=152: @(39)=146: @(40)=143
1036 @(41)=136: @(42)=134: @(43)=131
1038 STORE Z,2: PRINT '36-50 YEARS & ';: GOTO1060
1039 REM <36
1040 @(21)=164: @(22)=159: @(23)=153
1041 @(24)=149: @(25)=141: @(26)=140
1042 @(27)=138: @(29)=162: @(30)=157
1043 @(31)=151: @(32)=147: @(33)=139
1044 @(34)=138: @(35)=137: @(37)=169
1045 @(38)=164: @(39)=158: @(40)=154
1046 @(41)=146: @(42)=143: @(43)=140
1047 STORE Z,1: PRINT '<36 YEARS & ';: GOTO 1060
1049 REM >50
1050 @(21)=137: @(22)=133: @(23)=129
1051 @(24)=126: @(25)=120: @(26)=119
1052 @(27)=116: @(29)=135: @(30)=131
1053 @(31)=127: @(32)=124: @(33)=118
1054 @(34)=117: @(35)=115: @(37)=142
1055 @(38)=137: @(39)=133: @(40)=130
1056 @(41)=124: @(42)=122: @(43)=120
1057 STORE Z,3: PRINT '>50 YEARS & ';
1060 A=CHAN(1): IF A<64 GOTO 1070: REM CLOTHING FOR TEMP
1061 REM CP/DC
1062 @(20)=381: @(28)=379: @(36)=385: REM THRESHOLD TEMP'S x10
1063 STORE Z,2: PRINT 'DOUBLE COTTONS/PLASTICS': GOTO1080
1070 REM CC/WC
1071 @(20)=380: @(28)=378: @(36)=382: REM TEMP'S x10
1072 STORE Z,1: PRINT 'WORK CLOTHES/SINGLE COTTONS'
```

```
1080 REM INITIALIZE DATA ARRAY (ASSUMES HR-REST =75)
1085 FOR A=70 TO 161: @(A)=75: NEXT A: REM HR BUFFER
1090 FOR A=45 TO 51: @(A)=75: NEXT A: REM HR MTA'S
1095 FOR A=52 TO 60: @(A)=0: NEXT A: REM ALERT FLAGS
1096 @(61)=375: @(62)=750: @(63)=1500: REM MTA TOTALS
1097 @(64)=2250: @(65)=3375: @(66)=4500
1098 @(67)=6750: @(44)=360
1100 T=0: W=1: S=1: G=0: F=75: Y=6: P=0: R=0:  REM INITIALIZE OTHERS
1110 STORE Z,#2,999,999: REM PRESET ALERT TIMES TO 999
1120 PRINT: PRINT ' TIME   HR TEMP  ALERT LED BAT    QC'
1150 REM ******** END OF 1ST HALF MIN AFTER SLEEP *********
1155 REM IN RUN MODE, PROGRAM LOOPS BACK TO HERE
1160 SLEEP 3000 GOSUB10700: GOTO1160: REM INTERRUPT SERVICE
1161 IF S=0 PCLR2,3,4: REM LOW BATTERY: RESET IF ALERT GIVEN EARLIER
1162 IF S=4 PSET2,3,4: REM QUESTIONABLE HR DATA
1163 ?=0: REM RESET CLOCK VARIABLE FOR RECOVERY ROUTINE
1165 J=BAT: T=T+1: REM GET BAT VLT, INCR T EVERY 30 SECS
1170 GOSUB10000: GOSUB10400: REM GET & CHECK HR
1180 IF H>0 @(70)=H
1190 FOR A=1 TO 91: REM SHIFT HR BUFFER
1200 B=161-A: C=B+1
1210 @(C)=@(B)
1220 NEXT A
1230 IF P>0 GOSUB 10600: REM RECOVERY IN PROGRESS
1240 IF T=19 @(4)=@(4)+1: VSTORE @(4): REM INCR RUN COUNT @ 9.5 MIN
1270 IF J>70 R=0: GOTO 1300: REM BATTERY CHECK
1280 R=R+1: IF R<3 GOTO 1300: REM LOW BAT FOR <2 MIN - OK
1285 IF ((S=4)&(G>3)) GOTO 1300: REM  POOR HR QUALITY OVERRIDES
1290 IF S<>0 S=0: GOSUB10200: PCLR2,3,4: REM ALARM & CLEAR LEDS
1300 REM **** END OF 2ND HALF MIN AFTER THIS SLEEP ****
1310 SLEEP3000 GOSUB10700: GOTO1310
1315 ?=0: REM RESET CLOCK VARIABLE
1320 GOSUB10800: REM GET DISK TEMP
1330 T=T+1: REM FULL MIN AT THIS POINT
1340 GOSUB10000: GOSUB10400: REM GET AND CHECK HR
1350 IF H=0 H=@(71)
1355 @(70)=H: @(60)=G
1360 @(71)=(@(71)+H)/2: REM PUT PAST MIN HR INTO BUFFER
1370 @(44)=U: REM PLACE CURRENT DISK TEMP IN ARRAY
1375 REM CALCULATE NEW MTA'S
1380 @(61)=@(61)+@(71)-@(76): @(45)=@(61)/5
1381 @(62)=@(62)+@(71)-@(81): @(46)=@(62)/10
1382 @(63)=@(63)+@(71)-@(91): @(47)=@(63)/20
1383 @(64)=@(64)+@(71)-@(101): @(48)=@(64)/30
1384 @(65)=@(65)+@(71)-@(116): @(49)=@(65)/45
1385 @(66)=@(66)+@(71)-@(131): @(50)=@(66)/60
1386 @(67)=@(67)+@(71)-@(161): @(51)=@(67)/90
1400 V=W: REM STORE CURRENT ALERT STATUS
1410 REM LOOK FOR RESET FROM YEL (NOT RED) TO GRN
1420 E=0
1430 FOR A=1 TO 8
1440 B=A+27: C=A+43: D=A+51
1450 IF ((@(C)<=@(B))&(@(D)=1)) @(D)=0: REM PREVENTS RESET FROM RED
1460 IF @(D)=1 E=E+1
1470 NEXT A
1480 IF ((E=0)&(V=2)) W=1: REM DOUBLE CHECKS THAT STATUS WAS YEL
1500 REM LOOK FOR YEL TO RED
1510 E=0
1520 FOR A=1 TO 8
```

```
1530 B=A+35: C=A+43: D=A+51
1540 IF ((@(C)>=@(B))&(@(D)=1)) @(D)=2: REM ONLY YEL TO RED
1550 IF @(D)=2 E=E+1
1560 NEXT A
1570 IF E>0 W=3
1600 REM LOOK FOR GRN TO YEL FOR EACH VARIABLE
1620 E=0
1630 FOR A=1 TO 8
1640 B=A+19: C=A+43: D=51+A
1650 IF ((@(C)>=@(B))&(@(D)=0)) E=E+1: @(D)=1
1660 NEXT A
1670 IF ((E>0)&(V=1)) W=2
1700 REM UPDATE ALERT MODULE WITH RESULTS
1710 IF V=W GOTO1770: REM NO CHANGE
1730 IF ((S<>0)&(S<>4)) S=W: REM UPDATE ALERT STATUS
1740 PCLR 2,3,4
1750 GOSUB10200: REM ALARM
1760 A=W+1: PSETA: REM SET NEW LED
1763 IF A=3 B=4: STORE B,#2,T/2: REM STORE TIME OF LAST YEL ALERT
1764 IF A=4 B=2: STORE B,#2,T/2: REM STORE TIME OF RED ALERT
1770 REM STORE PREVIOUS FULL MINUTE DATA
1775 STORE Z,#2,T/2,#1,W,S,@(71),@(44)-300: REM TEMP TO 1 BYTE
1780 FOR A=0 TO 15: STORE Z, @(45+A): NEXT A
1783 STORE Z,J: REM STORE BAT VOLT
1785 Y=Z-1: REM PNTR TO LAST DATUM
1790 IF P>0 GOSUB10600: REM RECOVERY SERVICE
1795 PRINT#5,T/2,@(71),@(44),W,S,J,G: REM PRINT 1 MIN DATA
1800 GOTO 1160 : REM RETURN FOR NEXT HALF MIN
9000 REM
9010 REM   ******* SUBROUTINES *********
9020 REM
10000 REM ***** READ HR COUNTER *****
10001 REM ASSUMES 30 SECOND INTERVALS (DOUBLES CNTR VALUE)
10010 H=(PIN(11, 10, 9, 8, 7, 6, 5))*2: REM READ AND DOUBLE CNTR
10020 PSET13: I=1: GOSUB10300: PCLR13: REM RESET CNTR
10030 RETURN
10100 REM ***** ACKNOWLEDGE/RESET CMND BUTTON *****
10110 PSET 2,3,4,0: REM LIGHT LEDS AND CLEAR CMND SIGNAL
10120 A=PIN(1): IF A=1 GOTO10120: REM VERIFY CMND CLEAR
10130 I=1: GOSUB10300: A=PIN(1): IF A=1 GOTO10120
10135 REM RESET LED'S TO PREVIOUS STATE
10140 PCLR0,2,3,4: REM IF S=0, ALL REMAIN OFF
10141 IF S=1 PSET2
10142 IF S=2 PSET3
10143 IF S=3 PSET4
10144 IF S=4 PSET2,3,4
10154 RETURN
10200 REM ***** SET AUDIO ALARM ******
10210 PCLR12: I=1: GOSUB10300: PSET12: RETURN
10300 REM **** DELAY ROUTINE FOR I/100 SEC ****
10310 K=?+I: REM SET TIMER LIMIT
10320 IF ?<K GOTO10320: WAIT FOR LIMIT TO BE REACHED
10330 RETURN
10400 REM ***** HR QUALITY CHECK *****
10410 IF ((H>220)|(H<40)) G=G+1: H=0: GOTO10460: REM OUT OF RANGE
10420 A=((@(70))*13)/10: IF A>=H GOTO10440: REM INCREASE TOO FAST
10430 H=A: G=G+1: GOTO10460
10440 IF G>0 G=G-1: REM HR IS OK - TAKE CREDIT FROM COUNTER
10450 RETURN
```

```
10460 IF G<7 RETURN: REM NOT ENOUGH ?ABLE READINGS
10480 IF S=4 RETURN: REM ALARM HAS ALREADY BEEN GIVEN
10500 GOSUB10200: PSET2,3,4: S=4: REM ALARM & ALL LEDS ON
10510 RETURN
10600 REM ***** SERVICE RECOVERY HR *****
10605 IF P>3 GOTO10660: REM DELAYED NOTIFICATION DUE TO TIMING PROB
10610 IF Q>T RETURN: REM NOT TIME TO RECORD 30 SEC SAMPLE
10615 Q=T+2: A=161+P
10620 @(A)=@(70): P=P+1: REM STORE HR & INCREMENT PERIOD POINTER
10625 IF P<4 RETURN: REM NOT FINAL SAMPLE
10626 REM MAKE DECISION
10630 A=@(162)-@(164): REM P1-P3
10635 IF @(164)<90 P=4: GOTO10650: REM FULL
10640 IF (@(164)<120)&(A>10) P=5: GOTO10650: REM PARTIAL
10645 P=6: REM NO RECOVERY
10650 IF ?>1500 RETURN: REM NOT ENOUGH TIME TO SEND RESULT / WAIT
10660 REM FLASH RECOVERY DECISION FOR 15 SEC
10665 PCLR2,3,4: GOSUB10200: REM SEND AUDIO ALERT
10670 P=P-2
10675 FOR A=1 TO 7: REM FLASH APPROPRIATE LED
10676 PSETP: I=100: GOSUB10300: REM 1 SEC ON
10677 PCLRP: I=100: GOSUB10300: REM 1 SEC OFF
10678 NEXT A
10679 P=P-1: REM 1=GRN, 2=YEL, 3=RED FOR DATA STORAGE
10680 IF T=0 GOTO 10683: REM PRINT & STORE RESULTS (EXCEPT FOR DEMO)
10681 PRINT 'RECOVERY DATA: ',T/2,'.',(T%2)*5,#5,
      P,@(162),@(163),@(164)
10682 STORE Z,#2,999,#1, P, @(162), @(163), @(164): Y=Z-1
10683 P=0: REM RESET RECOVERY FLAG
10684 REM RESET LEDS TO ALERT STATUS
10691 IF S=0 RETURN
10692 IF S>3 PSET2,3,4: RETURN
10693 A=S+1: PSET A
10695 RETURN
10700 REM ***** SERVICE CMND BUTTON IN RUN *****
10710 GOSUB10100: REM ACKNOWLEDGE
10720 A=CHAN(2)
10730 IF A<192 GOTO150: REM STOP PM & GO TO CHECK (NEVER DUMP)
10745 REM RECOVERY REQUESTED -- OVERRIDES ANY CURRENT REQUEST
10750 Q=T+2+(?+1500)/3000: REM SYNC SAMPLE TO NEAREST HALF MINUTE
10760 A=Q-2: P=1: REM NOTE TIME & SET FLAG
10765 PRINT 'RECOVERY REQUEST AT ',A/2,'.',(A%2)*5, ' MIN'
10770 RETURN
10800 REM ****** TEMPERATURE ******
10810 REM T(DEG-C x1000)=INTRCP+SLOPE*(A/D READING)
10820 U=CHAN(5)
10825 U=@(0)+U*@(1): REM ACTUAL TEMPERATURE x1000
10830 U=U/100: REM TRUNCATED TO LOWER 1/10 DEGREE C
10840 RETURN
15000 REM         ***** DUMP ROUTINE *****
15001 GOSUB10200: PSET3,4: PCLR2: REM SOUND ALARM & SET YEL/RED
15002 GOSUB 15500: REM SET BAUD RATE & PRINT HEADER
15003 X=1: A=CHAN(3): REM READ DEMO/DUMP SWITCH
15007 IF A<64 X=0: REM  FULL OUTPUT, ELSE X=1 (SKIP MTA'S)
15009 PRINT 'SUMMARY OF PM ACTIVITY FOR RUN NUMBER ',@(4): PRINT
15010 Z=0: REM RESET STORAGE POINTER
15011 A=GET(Z): PRINT 'AGE BRACKET: ';: IF A=1 PRINT '<36'
15012 IF A=2 PRINT '36-50'
15013 IF A=3 PRINT '>50'
```

```
15014 A=GET(Z):PRINT 'CLOTHING: ';::IF A=1 PRINT 'WORK/SINGLE COTTONS'
15015 IF A=2 PRINT 'DOUBLE COTTONS/PLASTICS'
15016 PRINT: PRINT 'TIME OF RED/ACTION ALERT (min) = ', GET(Z,#2)
15017 PRINT 'TIME OF LAST YELLOW ALERT (min) = ', GET(Z,#2)
15018 PRINT 'PM RUN-TIME (min) = ',T/2
15020 PRINT : PRINT ' T   STATUS   HR  TEMP';
15021 IF X=C PRINT "                MTA's              ";
15022 PRINT '    FLAGS   QC BAT'
15025 PRINT 'min  A  L  bpm  Cx10';
15026 IF X=C PRINT '    1   2   3   4   5   6   7  ';
15027 PRINT "    T/MTA's    Vx10"
15030 IF Z>Y GOTO100: REM NO MORE DATA / LOOPS TO HERE
15031 SLEEPC: SLEEP 1 GOSUB10100: GOTO100: REM PAUSE FOR CMND INTRPT
15032 A=GET(Z,#2): IF A=999 GOTO15200: REM HR RECOVERY SUMMARY
15035 REM PRINT 1 MIN SUMMARY
15040 PRINT #3, A,GET(Z),GET(Z),#5,GET(Z),#6,(GET(Z)+300), ' ';
15045 IF X=1 Z=Z+7: GOTO15090: REM SKIP MTA'S
15050 FOR A=0 TO 6
15060 PRINT #4, GET (Z);
15070 NEXT A
15080 PRINT '   ';
15090 FOR A=1 TO 8
15100 PRINT #1, GET(Z);
15110 NEXT A
15115 PRINT #3, GET(Z), #4, GET(Z);
15120 PRINT ' ': REM SPACE/CR/LF AT END OF LINE
15150 GOTO15030
15200 PRINT "RECOVERY:";: REM ALERT STATUS AND P1,P2,P3
15210 FOR A=1 TO 4
15220 PRINT #4, GET(Z);
15230 NEXT A
15240 PRINT ' '
15270 GOTO15030
15300 REM ***** BAUD RATE SELECTION *****
15310 REM SELECTION SWITCH IS INSIDE THE MONITOR MODULE
15320 REM 8 BIT WORDS / 1 STOP BIT / NO PARITY
15330 A=CHAN(4): REM READ BAUD SELECTION
15340 IF A>196 UPROG '010010000500: REM 9600 BAUD
15350 IF (A<197)&(A>63) UPROG '010010000600: REM 1200 BAUD
15360 IF A<64 UPROG '010010000700: REM 300 BAUD
15370 RETURN
15400 REM **** LOOK FOR CONTROL CHARACTERS ****
15404 REM ^A STOPS PROGRAM
15406 REM INPUT BUFFER LOST
15410 B=Y+1: C=B: REM SET POINTER TO END OF DATA
15420 ITEXT B,1: REM GET INPUT BUFFER
15430 IF B=C RETURN: REM NOTHING THERE
15440 E=GET(C): REM GET CHAR
15450 IF E=1 GOTO 15470: REM ^A
15460 GOTO 15430: REM NEXT CHAR
15470 PRINT 'STOPPED': PSET0,2,3: PCLR0,4: STOP
15500 REM *** SET BAUD RATE & PRINT HEADER ***
15510 GOSUB 15300: REM BAUD RATE
15520 PRINT: PRINT 'EPRI PROTOTYPE PERSONAL MONITOR'
15530 PRINT: PRINT 'Westinghouse R&D Center - RP2705-5'
15540 PRINT 'Pennsylvania State University'
15550 PRINT '(c) 1987 Electric Power Research Institute, Inc'
15560 PRINT 'S/N: ', @(3),' / v3.1': PRINT: PRINT: RETURN
20000 REM
```

```
20001 REM ***** SPECIAL PURPOSE ROUTINES *****
20003 REM
21000 REM **** STORE FACTORS IN EEPROM ******
21005 VGET @(0): VGET @(1): VGET @(2)
21006 PRINT 'INTRCP = ', @(0), '    SLOPE = ', @(1)
21007 PRINT 'START BAT VOLT = ', @(2)
21008 PRINT 'IF DATA ARE OK, TYPE ^C & RTRN'
21010 INPUT 'INTERCEPT (DEG-C) x1000 = ' @(0)
21020 INPUT 'SLOPE (DEG-C / UNITS) x1000 = ' @(1)
21025 INPUT 'BATTERY STARTING VOLTAGE x10 = ' @(2)
21030 VSTORE @(0): VSTORE @(1): VSTORE @(2)
21040 VGET @(0): VGET @(1): VGET @(2)
21050 PRINT 'INTRCP = ', @(0), '    SLOPE = ', @(1)
21055 PRINT 'START BAT VOLT = ', @(2)
21060 STOP
21100 VGET @(0): VGET @(1)
21110 PRINT 'RUN NUMBER = ', @(4),'   S/N = ',@(3)
21120 INPUT 'RUN NUMBER = ' @(4): VSTORE @(4)
21130 INPUT 'S/N = ' @(3): VSTORE @(3)
21140 VGET @(4): VGET @(3)
21150 PRINT 'RUN NUMBER = ', @(4),'   S/N = ',@(3): STOP
30000 REM ***** DEEP SLEEP TO SAVE POWER *****
30010 PCLR2,3,4: PSET12: REM TURN-OFF LED'S & ALARM
30020 SLEEP0
30030 SLEEP1000 STOP: REM CMND RETURNS CONTROL
30040 GOTO30020: REM ALSO WAKE-UP WITH ^C
31000 REM ***** A/D CONVERTOR READINGS *****
31010 SLEEP 0: REM PRINTS 8 A/D CHANS & BAT EVERY 3 SEC
31020 FOR A=0TO7: PRINT#5,CHAN(A);: NEXT A
31030 PRINT #4, BAT
31040 SLEEP 300: GOTO31010
32000 REM ***** DEMONSTRATION OF ALERTS *****
32010 REM PRESENTS FOLLOWING ALERT PATTERN IN 5 SEC INTERVALS
32011 REM G-Y-G-Y-R THEN WAITS FOR CMND TO GIVE A YEL-RECOVERY
32020 REM RETURNS TO IDLE 10 SEC AFTER CMND OR RECOVERY
32022 REM GOES TO IDLE AFTER ANY CMND (EXCEPT IN RED)
32025 PRINT: PRINT 'ALERT DEMONSTRATION': REM ENTERS W/GRN
32030 SLEEP500 GOSUB 10100: GOTO100: REM WAIT 5 SEC
32040 GOSUB 10200: PCLR2: PSET3: REM SET YEL
32050 SLEEP500 GOSUB 10100: GOTO100
32060 GOSUB 10200: PCLR3: PSET2: REM SET GRN
32070 SLEEP500 GOSUB 10100: GOTO100
32080 GOSUB 10200: PCLR2: PSET3: REM SET YEL
32090 SLEEP500 GOSUB 10100: GOTO100
32100 GOSUB 10200: PCLR3: PSET4: REM SET RED
32105 T=0: S=3
32110 SLEEP1000 GOSUB 10100: GOTO32130: REM WAIT FOR CMND
32120 GOTO 100: REM NO CMND - RETURN
32130 SLEEP300: P=5: GOSUB 10600: REM YEL RECOVERY ALERT
32140 SLEEP0: SLEEP1000 GOSUB 10100: GOTO100: REM WAIT 10 SEC
32150 GOTO100: REM AND GO TO IDLE
```

What is claimed is:

1. A personal monitor for work and heat stress which comprises a heart beat sensor producing output electrical signals indicating a user's heart beats, means for storing heart beat information corresponding to the heart beat signals produced over predetermined time intervals, information processing means connected to receive the heart beat information from said storing means, said information processing means being configured to analyze the heart beat information incrementally over the predetermined time intervals through moving time averages with a plurality of different time bases to obtain a physiological demand during the predetermined time intervals and to compare the obtained physiological demand against a stored physiological demand limit, and means for providing an indication to the user when the stored physiological demand limit has been exceeded, said information processing means being configured and connected to control operation of said indication providing means.

2. The personal monitor for work and heat stress of claim 1 additionally comprising a an insulated skin temperature sensor configured to produce output electrical signals at least approximately indicating a user's body core temperature, said information processing means being connected to receive body core temperature information corresponding to the body core temperature output electrical signals, said information processing means further being configured to compare the body core temperature information against a stored body core temperature limit, said information processing means further being configured to cause said means for providing the indication to the user to provide the indication when the user's body core temperature exceeds the stored body core temperature limit.

3. The personal monitor for work and heat stress of claim 2 in which said insulated skin temperature sensor comprises a thermally and electrically conducting member having a surface configured to make direct contact with the user's skin, a device thermally connected to said thermally and electrically conducting member for producing an output electrical signal which is a function of temperature and a sufficient body of thermally insulating material surrounding a remainder of said thermally and electrically conducting member to provide the output electrical signal indicating insulated skin temperature as an approximation of body core temperature.

4. The personal monitor for work and heat stress of claim 3 in which said thermally and electrically conductive member additionally is connected as a ground electrode for said heart beat sensor.

5. The personal monitor for work and heat stress of claim 4 in which said thermally and electrically conducting member is a metal member.

6. The personal monitor for work and heat stress of claim 3 in which said thermally and electrically conducting member is a metal member.

7. The personal monitor for work and heat stress of claim 2 in which said monitor includes an input means for providing a user clothing type selection to said information processing means and said information processing means is further configured to select the body temperature limit based on the user clothing type selection for comparison with the body temperature information.

8. The personal monitor for work and heat stress of claim 1 in which said monitor includes an input means for providing a user age selection to said information processing means and said information processing means is further configured to select the stored physiological demand limit for the comparison based on the user age selection.

9. The personal monitor for work and heat stress of claim 1 in which said monitor includes an input means for user selection of an operation mode, and said information processing means is further configured to record user heart beat rates for a plurality of intervals and to compare the user heart beat rate for at least one of the intervals in response to user selection of an operation mode and to provide an indication of the comparison to the user.

10. The personal monitor for work and heat stress of claim 9 in which said information processing means is further configured to compare the user heart beat rate for a last of the intervals against a predetermined limit and to provide an indication of the comparison to the user.

11. A temperature sensor comprising a thermally and electrically conducting member having a bare, outwardly facing, unbroken surface configured and positioned to make direct contact with the skin of a person whose temperature is to be measured, a temperature sensitive solid state device thermally and electrically directly connected to an opposite surface of said thermally and electrically conducting member for producing an output electrical signal which is a function of temperature and a sufficient body of thermally insulating material surrounding a remainder of said thermally and electrically conducting member to provide the output electrical signal indicating insulated skin temperature as an approximation of the person's body core temperature, said thermally and electrically conducting member comprising both a thermal contact for the person's skin and a reference electrode of said temperature sensor.

12. The temperature sensor of claim 11 in which said body of thermally insulating material comprises a foamed plastic.

13. The temperature sensor of claim 11 in which said thermally and electrically conducting member is a metal member.

14. A process for monitoring heat and work stress of an individual, which comprises measuring the individual's heart beats over predetermined time intervals, analyzing the heart beat information incrementally over the predetermined time intervals through moving time averages with a plurality of different time bases to obtain a physiological demand during the predetermined time intervals, comparing the obtained physiological demand against a predetermined physiological demand limit, and providing an indication to the individual when the predetermined physiological demand limit has been exceeded.

15. The process for monitoring heat and work stress of an individual of claim 14, additionally comprising the steps of measuring the individual's insulated skin temperature as an approximation of body core temperature during the predetermined time intervals, comparing the measured approximation of body core temperature against a predetermined temperature limit and providing an indication to the individual when the measured approximation of body core temperature exceeds the predetermined temperature limit.

16. The process of claim 15 in which the approximation of body core temperature is measured by contacting the individual's skin with a surface configured to make direct contact with the user's skin of a thermally and electrically conducting member, insulating a remainder of the thermally and electrically conducting member, and producing an output electrical signal which is a function of temperature of the thermally and electrically conducting member.

17. The process of claim 16 in which the thermally and electrically conducting member is a metal member.

18. The process of claim 15 additionally comprising the step of selecting the predetermined temperature limit based on a clothing type for the individual.

19. The process of claim 14 additionally comprising the step of selecting the physiological demand limit based on the individual's age.

* * * * *